(12) United States Patent
Gil et al.

(10) Patent No.: US 12,415,269 B2
(45) Date of Patent: *Sep. 16, 2025

(54) KINEMATIC STRUCTURES FOR ROBOTIC MICROSURGICAL PROCEDURES

(71) Applicant: ForSight Robotics Ltd., Yokneam Illit (IL)

(72) Inventors: Ariel Gil, Haifa (IL); Daniel Glozman, Kfar Yona (IL); Ofer Arnold, Ma'ale Zvia (IL)

(73) Assignee: ForSight Robotics Ltd., Yokneam Illit (IL)

( * ) Notice: Subject to any disclaimer, the term of this patent is extended or adjusted under 35 U.S.C. 154(b) by 375 days.

This patent is subject to a terminal disclaimer.

(21) Appl. No.: 18/126,095

(22) Filed: Mar. 24, 2023

(65) Prior Publication Data

US 2023/0233204 A1 Jul. 27, 2023

Related U.S. Application Data

(63) Continuation of application No. PCT/IB2022/055086, filed on May 31, 2022.
(Continued)

(51) Int. Cl.
*B25J 9/16* (2006.01)
*A61B 17/00* (2006.01)
(Continued)

(52) U.S. Cl.
CPC .......... *B25J 9/1628* (2013.01); *A61B 17/072* (2013.01); *A61B 34/30* (2016.02); *A61B 34/37* (2016.02); *A61B 46/10* (2016.02); *A61B 46/40* (2016.02); *B25J 9/102* (2013.01); *A61B 2017/00398* (2013.01)

(58) Field of Classification Search
None
See application file for complete search history.

(56) References Cited

U.S. PATENT DOCUMENTS

| | | |
|---|---|---|
| 5,269,787 A | 12/1993 | Cozean et al. |
| 5,410,638 A | 4/1995 | Colgate et al. |

(Continued)

FOREIGN PATENT DOCUMENTS

| | | |
|---|---|---|
| CN | 109602498 A | 4/2019 |
| CN | 109602499 A | 4/2019 |

(Continued)

OTHER PUBLICATIONS

Non-Final Office Action for U.S. Appl. No. 17/818,477 mailed Dec. 5, 2023.
(Continued)

*Primary Examiner* — Michael W Kahelin
(74) *Attorney, Agent, or Firm* — Dorsey & Whitney LLP

(57) ABSTRACT

Apparatus and methods are described for performing a procedure using a robotic unit. A tool-actuation arm is driven to move linearly, to thereby move at least the portion of the tool linearly with respect to the end effector. The tool-actuation arm is driven to become retracted to a given distance from the tool mount, thereby causing the tool-actuation arm to fold automatically by actuating an automatic tool-actuation arm folding mechanism. Other applications are also described.

14 Claims, 17 Drawing Sheets

Related U.S. Application Data

(60) Provisional application No. 63/229,593, filed on Aug. 5, 2021, provisional application No. 63/195,429, filed on Jun. 1, 2021.

(51) Int. Cl.
*A61B 17/072* (2006.01)
*A61B 34/30* (2016.01)
*A61B 34/37* (2016.01)
*A61B 46/00* (2016.01)
*A61B 46/10* (2016.01)
*B25J 9/10* (2006.01)

(56) References Cited

U.S. PATENT DOCUMENTS

| | | |
|---|---|---|
| 5,828,197 A | 10/1998 | Martin et al. |
| 7,896,653 B2 | 3/2011 | Nylen |
| 8,396,598 B2 | 3/2013 | Sutherland et al. |
| 8,509,949 B2 | 8/2013 | Bordyn et al. |
| 8,512,353 B2 | 8/2013 | Rosielle |
| 8,596,789 B2 | 12/2013 | Takii |
| 8,690,212 B2 | 4/2014 | Lee et al. |
| 9,039,681 B2 | 5/2015 | Wang et al. |
| 9,283,043 B2 | 3/2016 | Tsao et al. |
| 9,358,078 B2 | 6/2016 | Lim et al. |
| 9,383,832 B1 | 7/2016 | Lammertse |
| 9,504,604 B2 | 11/2016 | Alvarez |
| 9,655,681 B2 | 5/2017 | Meenink |
| 9,658,605 B2 | 5/2017 | Lee et al. |
| 9,788,910 B2 | 10/2017 | Schuh |
| 9,835,849 B2 | 12/2017 | Schneider et al. |
| 9,918,066 B2 | 3/2018 | Schneider et al. |
| 9,943,708 B2 | 4/2018 | Roberts et al. |
| 9,967,475 B2 | 5/2018 | Schneider et al. |
| 9,993,313 B2 | 6/2018 | Schuh et al. |
| 10,073,515 B2 | 9/2018 | Awdeh |
| 10,149,720 B2 | 12/2018 | Romo |
| 10,345,582 B2 | 7/2019 | Schneider et al. |
| 10,433,916 B2 | 10/2019 | Schneider et al. |
| 10,507,067 B2 | 12/2019 | Glozman et al. |
| 10,582,975 B2 | 3/2020 | Simi et al. |
| 10,631,949 B2 | 4/2020 | Schuh et al. |
| 10,722,312 B2 | 7/2020 | Marshall et al. |
| 10,744,035 B2 | 8/2020 | Alvarez et al. |
| 10,779,727 B2 | 9/2020 | Zeitouny et al. |
| 10,786,323 B2 | 9/2020 | Ang et al. |
| 10,806,523 B2 | 10/2020 | Roth et al. |
| 10,821,046 B2 | 11/2020 | Hares et al. |
| 10,864,051 B2 | 12/2020 | Simi et al. |
| 10,888,384 B2 | 1/2021 | Rosielle et al. |
| 10,895,742 B2 | 1/2021 | Schneider et al. |
| 10,895,750 B2 | 1/2021 | Schneider et al. |
| 10,932,865 B2 | 3/2021 | Zhang et al. |
| 11,013,565 B2 | 5/2021 | Beelen et al. |
| 11,039,891 B2 | 6/2021 | Shochat et al. |
| 11,058,574 B2 | 7/2021 | Michels et al. |
| 11,083,488 B2 | 8/2021 | Galili et al. |
| 11,090,747 B2 | 8/2021 | Simi et al. |
| 11,096,748 B2 | 8/2021 | Simi et al. |
| 11,103,319 B2 | 8/2021 | Simi et al. |
| 11,129,686 B2 | 9/2021 | Chaplin et al. |
| 11,141,233 B2 | 10/2021 | Simi et al. |
| 11,154,371 B2 | 10/2021 | Jackson et al. |
| 11,202,684 B2 | 12/2021 | Arnold et al. |
| 11,389,249 B2 | 7/2022 | Schneider et al. |
| 11,471,169 B1 | 10/2022 | Nikou et al. |
| 11,484,363 B2 | 11/2022 | Schneider et al. |
| 11,523,839 B2 | 12/2022 | Wellman et al. |
| 11,551,582 B2 | 1/2023 | Slabber et al. |
| 11,800,966 B2 | 10/2023 | Kihara et al. |
| 11,957,421 B2 | 4/2024 | Shelton et al. |
| 2001/0020200 A1 | 9/2001 | Das et al. |
| 2003/0125716 A1 | 7/2003 | Wang et al. |
| 2004/0092982 A1 | 5/2004 | Sheffer |
| 2006/0142897 A1 | 6/2006 | Green |
| 2007/0191862 A1 | 8/2007 | Ellis |
| 2007/0299427 A1 | 12/2007 | Yeung et al. |
| 2010/0137880 A1 | 6/2010 | Nahum et al. |
| 2010/0331858 A1 | 12/2010 | Chang et al. |
| 2011/0054315 A1 | 3/2011 | Roberts et al. |
| 2011/0306986 A1 | 12/2011 | Lee et al. |
| 2012/0071863 A1 | 3/2012 | Lee et al. |
| 2012/0162076 A1 | 6/2012 | Obermeyer et al. |
| 2013/0035537 A1 | 2/2013 | Wallace et al. |
| 2013/0131867 A1 | 5/2013 | Olds et al. |
| 2014/0114480 A1 | 4/2014 | Greer et al. |
| 2014/0142591 A1 | 5/2014 | Alvarez et al. |
| 2014/0166023 A1 | 6/2014 | Kishi |
| 2014/0194699 A1 | 7/2014 | Roh et al. |
| 2014/0194859 A1 | 7/2014 | Ianchulev |
| 2014/0364870 A1 | 12/2014 | Alvarez et al. |
| 2015/0202009 A1 | 7/2015 | Nussbaumer et al. |
| 2015/0257841 A1 | 9/2015 | Dachs |
| 2015/0265807 A1 | 9/2015 | Park et al. |
| 2015/0335480 A1 | 11/2015 | Alvarez et al. |
| 2016/0063898 A1 | 3/2016 | Bernal |
| 2016/0157941 A1* | 6/2016 | Anvari ................ A61B 34/70 |
| | | 279/143 |
| 2016/0270867 A1 | 9/2016 | Scholan |
| 2016/0346060 A1 | 12/2016 | Nawrat et al. |
| 2017/0252208 A1 | 9/2017 | Meenink |
| 2018/0042682 A1 | 2/2018 | Iceman et al. |
| 2018/0104013 A1 | 4/2018 | Hamamoto et al. |
| 2018/0147017 A1 | 5/2018 | Marshall et al. |
| 2018/0200008 A1 | 7/2018 | Cooper |
| 2018/0296285 A1 | 10/2018 | Simi et al. |
| 2018/0303567 A1 | 10/2018 | Simi et al. |
| 2018/0319023 A1 | 11/2018 | Robinson et al. |
| 2018/0360654 A1 | 12/2018 | Michels et al. |
| 2019/0000706 A1 | 1/2019 | Hares et al. |
| 2019/0038369 A1 | 2/2019 | Naus et al. |
| 2019/0099232 A1 | 4/2019 | Soto et al. |
| 2019/0125582 A1 | 5/2019 | Marchini |
| 2019/0223977 A1 | 7/2019 | Galili et al. |
| 2019/0314529 A1 | 10/2019 | Mordaunt |
| 2019/0336222 A1 | 11/2019 | Schneider et al. |
| 2019/0343594 A1 | 11/2019 | Garcia Kilroy et al. |
| 2020/0008890 A1 | 1/2020 | Seneci et al. |
| 2020/0015917 A1 | 1/2020 | Cavalier et al. |
| 2020/0046394 A1 | 2/2020 | Cau |
| 2020/0170740 A1 | 6/2020 | Galili et al. |
| 2020/0222124 A1 | 7/2020 | Savall et al. |
| 2020/0237467 A1 | 7/2020 | Savall et al. |
| 2020/0261169 A1 | 8/2020 | Miller et al. |
| 2020/0323427 A1 | 10/2020 | Gharib et al. |
| 2020/0346046 A1 | 11/2020 | Cannata et al. |
| 2020/0360092 A1 | 11/2020 | Deng et al. |
| 2020/0360095 A1 | 11/2020 | Grant et al. |
| 2020/0397520 A1 | 12/2020 | Penny et al. |
| 2020/0397531 A1 | 12/2020 | Schrader et al. |
| 2020/0405403 A1 | 12/2020 | Shelton et al. |
| 2021/0000558 A1 | 1/2021 | Penny et al. |
| 2021/0015573 A1 | 1/2021 | Tsao et al. |
| 2021/0015574 A1 | 1/2021 | Atay et al. |
| 2021/0030499 A1 | 2/2021 | Peine |
| 2021/0045828 A1 | 2/2021 | McBrien et al. |
| 2021/0059776 A1 | 3/2021 | Simi et al. |
| 2021/0068911 A1 | 3/2021 | Walker et al. |
| 2021/0095405 A1 | 4/2021 | Ren et al. |
| 2021/0106393 A1 | 4/2021 | Simi et al. |
| 2021/0121256 A1 | 4/2021 | Simi et al. |
| 2021/0121259 A1 | 4/2021 | Simi et al. |
| 2021/0121264 A1 | 4/2021 | Tadano et al. |
| 2021/0137618 A1 | 5/2021 | Simi et al. |
| 2021/0142696 A1 | 5/2021 | Omata et al. |
| 2021/0145530 A1 | 5/2021 | Martin |
| 2021/0186636 A1 | 6/2021 | Gunn et al. |
| 2021/0196417 A1 | 7/2021 | Simi et al. |
| 2021/0205039 A1 | 7/2021 | Simi et al. |
| 2021/0228292 A1 | 7/2021 | Tsao et al. |
| 2021/0268663 A1 | 9/2021 | Gu et al. |
| 2021/0339326 A1 | 11/2021 | Simi et al. |
| 2021/0339327 A1 | 11/2021 | Simi et al. |

(56) References Cited

U.S. PATENT DOCUMENTS

| | | |
|---|---|---|
| 2021/0339328 A1 | 11/2021 | Simi et al. |
| 2021/0369374 A1 | 12/2021 | Simi et al. |
| 2021/0386495 A1 | 12/2021 | Simi et al. |
| 2021/0386496 A1 | 12/2021 | Simi et al. |
| 2021/0401522 A1 | 12/2021 | Mantri et al. |
| 2022/0000540 A1 | 1/2022 | Grover |
| 2022/0022983 A1 | 1/2022 | Arnold et al. |
| 2022/0071718 A1 | 3/2022 | Fukuno et al. |
| 2022/0079808 A1 | 3/2022 | Gliner et al. |
| 2022/0104892 A1 | 4/2022 | Hufford et al. |
| 2022/0249183 A1 | 8/2022 | Charles |
| 2022/0378613 A1 | 12/2022 | Glozman et al. |
| 2023/0070830 A1 | 3/2023 | Simi et al. |
| 2023/0142530 A1 | 5/2023 | Hipsley et al. |
| 2023/0190399 A1 | 6/2023 | Spuhler et al. |
| 2023/0226685 A1 | 7/2023 | Gil et al. |

FOREIGN PATENT DOCUMENTS

| | | |
|---|---|---|
| DE | 4012882 A1 | 10/1991 |
| EP | 3370198 A1 | 9/2018 |
| EP | 3658057 B1 | 8/2023 |
| FR | 3109717 A1 | 11/2021 |
| GB | 2605812 A | 10/2022 |
| JP | 2019530517 A | 10/2019 |
| KR | 101400447 B1 | 5/2014 |
| WO | 2009097539 A2 | 8/2009 |
| WO | 2009120945 A1 | 10/2009 |
| WO | 2009120948 A2 | 10/2009 |
| WO | 2011088400 A2 | 7/2011 |
| WO | 2011100657 A1 | 8/2011 |
| WO | 2013090598 A1 | 6/2013 |
| WO | 2013101269 A1 | 7/2013 |
| WO | 2014004114 A1 | 1/2014 |
| WO | 2014197889 A1 | 12/2014 |
| WO | 2014201165 A1 | 12/2014 |
| WO | 2015010189 A1 | 1/2015 |
| WO | 2016054256 A1 | 4/2016 |
| WO | 2017044965 A1 | 3/2017 |
| WO | 2017064306 A1 | 4/2017 |
| WO | 2017134077 A1 | 8/2017 |
| WO | 2017179044 A1 | 10/2017 |
| WO | 2017214243 A1 | 12/2017 |
| WO | 2018020251 A1 | 2/2018 |
| WO | 2018142397 A1 | 8/2018 |
| WO | 2018153512 A1 | 8/2018 |
| WO | 2018157078 A1 | 8/2018 |
| WO | 2019183106 A1 | 9/2019 |
| WO | 2019183236 A1 | 9/2019 |
| WO | 2019209967 A1 | 10/2019 |
| WO | 2019212018 A1 | 11/2019 |
| WO | 2019222228 A1 | 11/2019 |
| WO | 2020070501 A1 | 4/2020 |
| WO | 2020084611 A1 | 4/2020 |
| WO | 2020084625 A1 | 4/2020 |
| WO | 2020099192 A1 | 5/2020 |
| WO | 2020141487 A2 | 7/2020 |
| WO | 2020154012 A1 | 7/2020 |
| WO | 2021105703 A1 | 6/2021 |
| WO | 2021105992 A1 | 6/2021 |
| WO | 2021105993 A1 | 6/2021 |
| WO | 2021140513 A1 | 7/2021 |
| WO | 2021178961 A1 | 9/2021 |
| WO | 2021213751 A1 | 10/2021 |
| WO | 2021213851 A1 | 10/2021 |
| WO | 2021214750 A1 | 10/2021 |
| WO | 2021214751 A1 | 10/2021 |
| WO | 2021214754 A1 | 10/2021 |
| WO | 2021219311 A1 | 11/2021 |
| WO | 2021258007 A1 | 12/2021 |
| WO | 2022023962 A2 | 2/2022 |
| WO | 2022034488 A1 | 2/2022 |
| WO | 2022233585 A1 | 11/2022 |
| WO | 2022254335 A1 | 12/2022 |
| WO | 2023062470 A1 | 4/2023 |
| WO | 2023100123 A1 | 6/2023 |
| WO | 2023100124 A1 | 6/2023 |
| WO | 2023100125 A1 | 6/2023 |
| WO | 2023100126 A1 | 6/2023 |
| WO | 2023205761 A2 | 10/2023 |
| WO | 2023209550 A1 | 11/2023 |
| WO | 2024074948 A1 | 4/2024 |
| WO | 2024097895 A1 | 5/2024 |
| WO | 2024127205 A1 | 6/2024 |
| WO | 2024148299 A1 | 7/2024 |
| WO | 2024148316 A2 | 7/2024 |
| WO | 2024148331 A2 | 7/2024 |
| WO | 2024148334 A2 | 7/2024 |
| WO | 2024176143 A1 | 8/2024 |
| WO | 2024201236 | 10/2024 |
| WO | 2024231879 A1 | 11/2024 |

OTHER PUBLICATIONS

Non-Final Office Action for U.S. Appl. No. 18/125,922 mailed May 14, 2025.
Restriction Requirement for U.S. Appl. No. 18/125,489 mailed May 19, 2025.
Restriction Requirement for U.S. Appl. No. 18/298,490 mailed Apr. 9, 2025.
International Search Report and Written Opinion from International Application No. PCT/IB2023/054217 mailed Sep. 25, 2023.
Invitation to Pay Additional Fees for International Application No. PCT/IB2023/054217 mailed Aug. 2, 2023.
Non-Final Office Action for U.S. Appl. No. 17/818,477 mailed Dec. 5, 2024.
Extended European Search Report for European Application No. 24163523.4 mailed Jun. 27, 2024.
Final Office Action for U.S. Appl. No. 17/818,477 mailed Mar. 26, 2025.
International Search Report and Written Opinion from International Application No. PCT/IB2024/051675 mailed Jul. 15, 2024.
International Search Report and Written Opinion from International Application No. PCT/IB2024/052760 mailed Aug. 20, 2024.
International Search Report and Written Opinion from International Application No. PCT/IB2024/054525 mailed Sep. 16, 2024.
Invitation to Pay Additional Fees for International Application No. PCT/IB2024/051675 mailed May 23, 2024.
Invitation to Pay Additional Fees for International Application No. PCT/IB2024/052760 mailed Jun. 28, 2024.
Invitation to Pay Additional Fees for International Application No. PCT/IB2024/054525 mailed Jul. 25, 2024.
Non-Final Office Action for U.S. Appl. No. 17/818,477 mailed Dec. 2, 2024.
Non-Final Office Action for U.S. Appl. No. 18/004,907 mailed Mar. 5, 2025.
Non-Final Office Action for U.S. Appl. No. 18/298,891 mailed Mar. 10, 2025.
U.S. Appl. No. 18/822,932, filed Sep. 3, 2024.
U.S. Appl. No. 18/825,382, filed Sep. 5, 2024.
U.S. Appl. No. 18/860,829, filed Oct. 28, 2024.
U.S. Appl. No. 19/097,061, filed Apr. 1, 2025.
U.S. Appl. No. 63/335,751, filed Apr. 28, 2022.
U.S. Appl. No. 63/412,475, filed Oct. 2, 2022.
U.S. Appl. No. 63/536,772, filed Sep. 6, 2023.
U.S. Appl. No. 63/537,053, filed Sep. 7, 2023.
Communication Pursuant to Article 94(3) EPC for European Application No. 21749334.5 mailed Jun. 2, 2023.
Final Office Action for U.S. Appl. No. 17/818,477 mailed Jul. 6, 2023.
International Search Report and Written Opinion from International Application No. PCT/IB2022/059386 mailed Jan. 3, 2023.
International Search Report and Written Opinion from International Application No. PCT/IB2022/061633 mailed Apr. 6, 2023.
International Search Report and Written Opinion from International Application No. PCT/IB2022/061634 mailed Feb. 15, 2023.
International Search Report and Written Opinion from International Application No. PCT/IB2022/061635 mailed Apr. 14, 2023.

(56) References Cited

OTHER PUBLICATIONS

International Search Report and Written Opinion from International Application No. PCT/IB2022/061636 mailed Feb. 24, 2023.
Invitation to Pay Additional Fees for International Application No. PCT/IB2022/061633 mailed Feb. 15, 2023.
Invitation to Pay Additional Fees for International Application No. PCT/IB2022/061635 mailed Feb. 22, 2023.
U.S. Appl. No. 18/298,490, filed Apr. 11, 2023.
U.S. Appl. No. 18/298,891, filed Apr. 11, 2023.
U.S. Appl. No. 63/256,587, filed Oct. 17, 2021.
U.S. App. No. 63/285,185 filed Dec. 2, 2021.
U.S. Appl. No. 63/285,218, filed Dec. 2, 2021.
U.S. Appl. No. 63/406,881, filed Sep. 15, 2022.
Communication Pursuant to Article 94(3) EPC for European Application No. 22727496.6 mailed Jun. 23, 2023.
International Search Report and Written Opinion from International Application No. PCT/IB2022/061635 mailed Jul. 3, 2023.
Final Office Action for U.S. Appl. No. 17/818,477 mailed Jul. 9, 2024.
International Search Report and Written Opinion from International Application No. PCT/IB2023/059694 mailed Dec. 22, 2023.
International Search Report and Written Opinion from International Application No. PCT/IB2023/062467 mailed May 2, 2024.
Invitation to Pay Additional Fees for International Application No. PCT/IB2023/062467 mailed Mar. 5, 2024.
U.S. Appl. No. 18/714,024, filed May 28, 2024.
U.S. Appl. No. 18/714,027, filed May 28, 2024.
U.S. Appl. No. 63/285,147, filed Dec. 2, 2021.
Communication Pursuant to Article 94(3) EPC for European Patent Application No. 21749334.5 mailed Dec. 14, 2022.
Examination Report for European Application No. 21749334.5 mailed Dec. 14, 2022.
International Search Report and Written Opinion from Intenational Application No. PCT/IB2022/055086 mailed Nov. 22, 2022.
International Search Report and Written Opinion from International Application No. PCT/IB2021/056784 mailed Feb. 14, 2022.
International Search Report and Written Opinion from International Application No. PCT/IB2021/057353 mailed Jan. 13, 2022.
International Search Report and Written Opinion from International Application No. PCT/IB2021/057353 mailed May 3, 2022.
Invitation to Pay Additional Fees for International Application No. PCT/IB2021/056784 mailed Oct. 27, 2021.
Invitation to Pay Additional Fees for International Application No. PCT/IB2021/057353 mailed Nov. 22, 2021.
Invitation to Pay Additional Fees for International Application No. PCT/IB2022/055086 mailed Sep. 1, 2022.
Non-Final Office Action for U.S. Appl. No. 17/818,477 mailed Mar. 2, 2023.
U.S. Appl. No. 17/818,477, filed Aug. 9, 2022.
U.S. Appl. No. 18/004,907, filed Jan. 10, 2023.
U.S. Appl. No. 18/095,267, filed Jan. 10, 2023.
U.S. Appl. No. 18/095,630, filed Jan. 11, 2023.
U.S. Appl. No. 18/125,489, filed Mar. 23, 2023.
U.S. Appl. No. 18/125,922, filed Mar. 24, 2023.
U.S. Appl. No. 63/057,391, filed Jul. 28, 2020.
U.S. Appl. No. 63/065,068, filed Aug. 13, 2020.
U.S. Appl. No. 63/087,408, filed Oct. 5, 2020.
U.S. Appl. No. 63/195,429, filed Jun. 1, 2021.
U.S. Appl. No. 63/229,593, filed Aug. 5, 2021.
Boctor, et al., "Virtual Remote Center of Motion control for needle placement robots", Computer Aided Surgery; 9(5), 2004, pp. 175-183.
Chen, et al., "Semiautomated optical coherence tomography-guided robotic surgery for porcine lens removal", Laboratory Science: Robotic Surgery for Lens Extraction in an Animal Model, vol. 45 Issue 11, pp. 1665-1669, Nov. 2019.
Emeagwali, et al., "Performance Analysis of Steady-Hand Teleoperation versus Cooperative Manipulation", Research Gate, Conference Paper, Mar. 2004, pp. 1-7.
Mitchell, et al., "Development and Application of a New Steady-Hand Manipulator for Retinal Surgery", Proceedings 2007 IEEE International Conference on Robotics and Automation, pp. 623-629, 2007.
Wilson, et al., "Intraocular robotic interventional surgical system (IRISS): Mechanical design, evaluation, and master-slave manipulation", The International Journal of Medical Robotics and Computer Assisted Surgery,, pp. 1-12, 2018.

\* cited by examiner

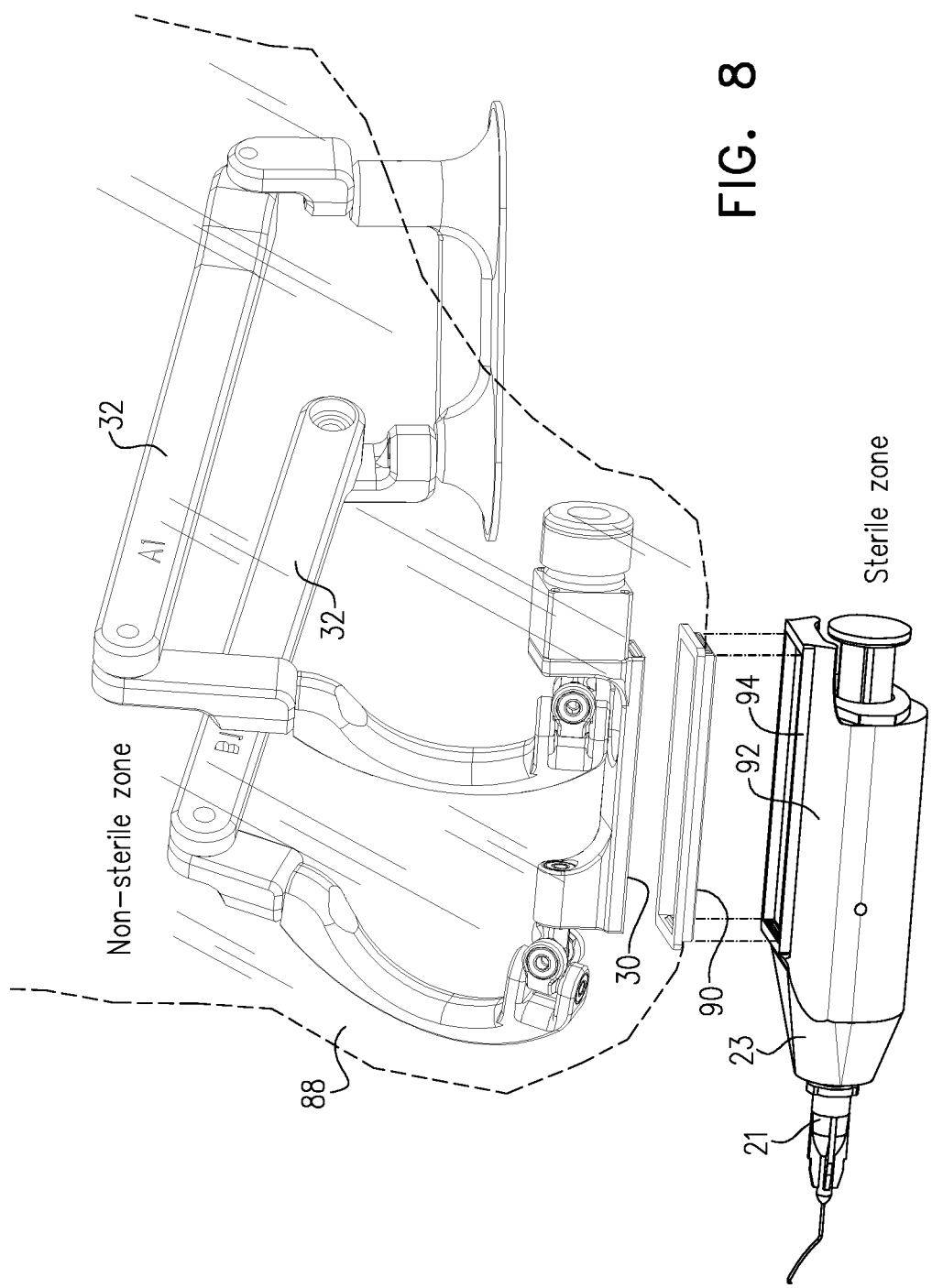

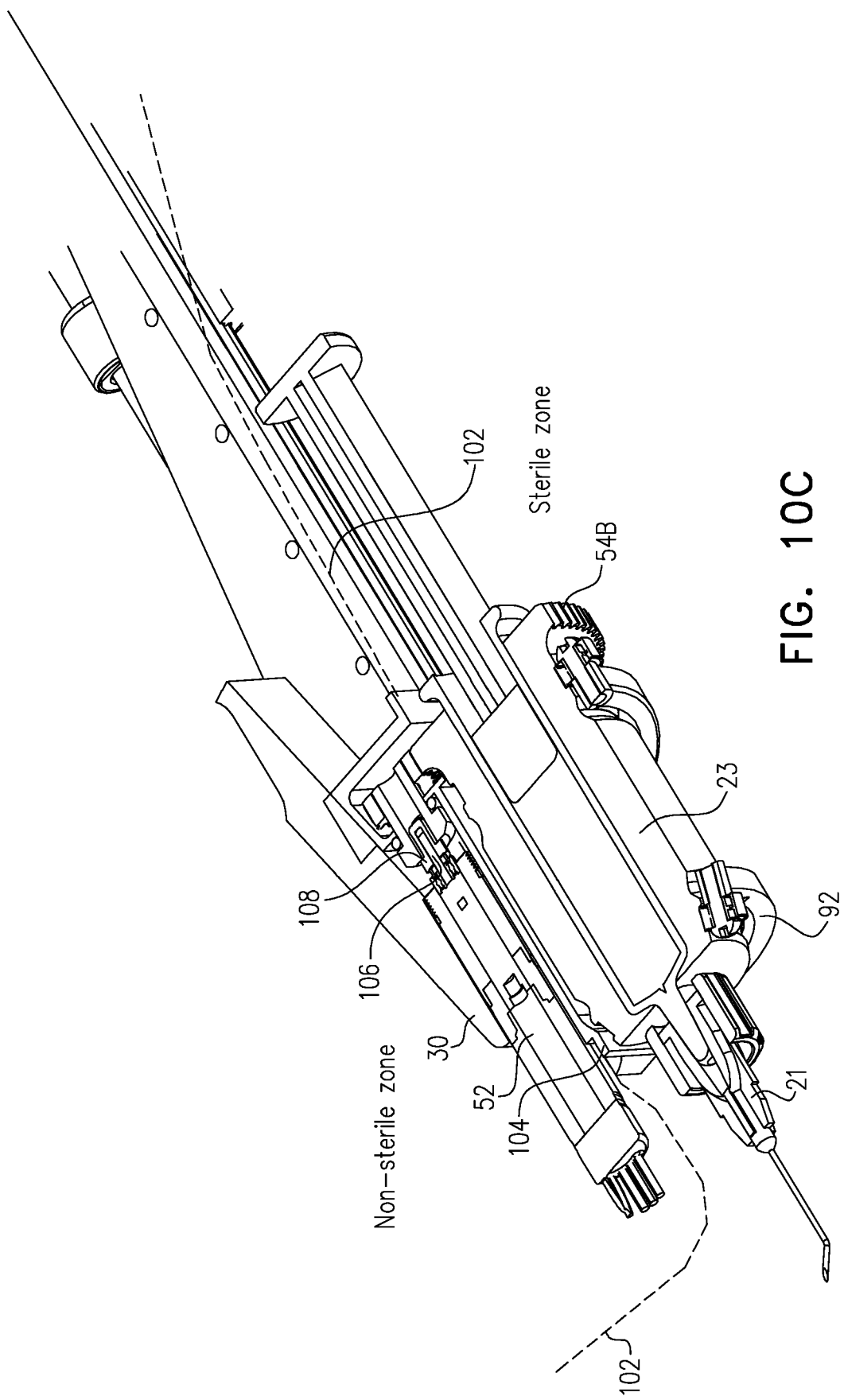

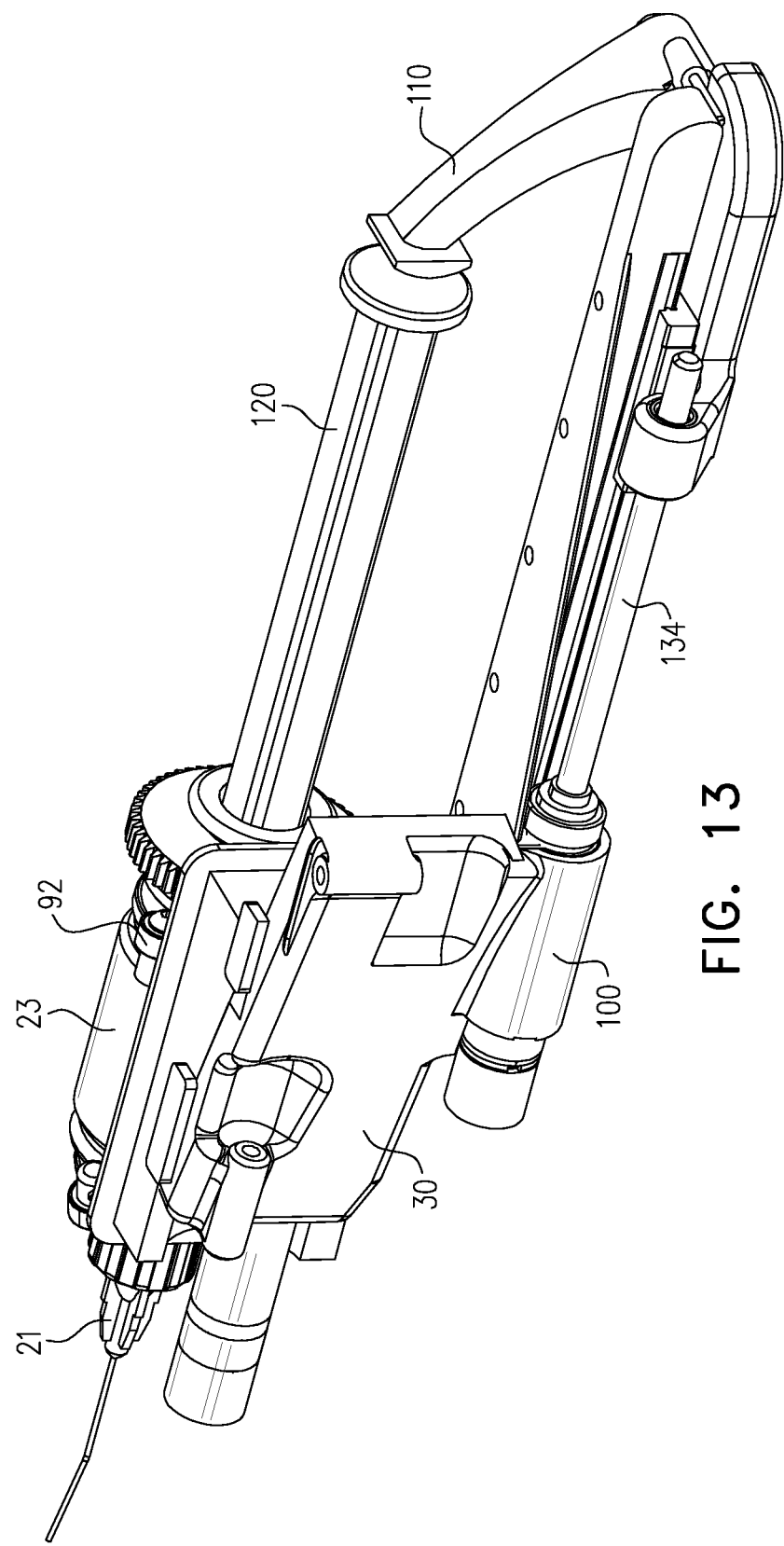

KINEMATIC STRUCTURES FOR ROBOTIC MICROSURGICAL PROCEDURES

CROSS-REFERENCE TO RELATED APPLICATIONS

The present application is a continuation of PCT application no. PCT/IB2022/055086 to Gil et al. filed May 31, 2022, entitled "Kinematic structures and sterile drapes for robotic microsurgical procedures" (published as WO 22/254335), which claims priority from:
U.S. Provisional Patent Application No. 63/195,429 to Gil et al., filed Jun. 1, 2021, entitled "Kinematic structures for robotic microsurgical procedures," and
U.S. Provisional Patent Application No. 63/229,593 to Gil et al., filed Aug. 5, 2021, entitled "Sterile drapes for robotic microsurgical procedures."
Both of the above-referenced U.S. Provisional applications are incorporated herein by reference.

FIELD OF EMBODIMENTS OF THE INVENTION

Some applications of the present invention generally relate to medical apparatus and methods. Specifically, some applications of the present invention relate to apparatus and methods for performing microsurgical procedures in a robotic manner.

BACKGROUND

Cataract surgery involves the removal of the natural lens of the eye that has developed an opacification (known as a cataract), and its replacement with an intraocular lens. Such surgery typically involves a number of standard steps, which are performed sequentially.

In an initial step, the patient's face around the eye is disinfected (typically, with iodine solution), and their face is covered by a sterile drape, such that only the eye is exposed. When the disinfection and draping has been completed, the eye is anesthetized, typically using a local anesthetic, which is administered in the form of liquid eye drops. The eyeball is then exposed, using an eyelid speculum that holds the upper and lower eyelids open. One or more incisions (and typically two or three incisions) are made in the cornea of the eye. The incision(s) are typically made using a specialized blade, which is called a keratome blade. At this stage, lidocaine is typically injected into the anterior chamber of the eye, in order to further anesthetize the eye. Following this step, a viscoelastic injection is applied via the corneal incision(s). The viscoelastic injection is performed in order to stabilize the anterior chamber and to help maintain eye pressure during the remainder of the procedure, and also in order to distend the lens capsule.

In a subsequent stage, known as capsulorhexis, a part of the anterior lens capsule is removed. Various enhanced techniques have been developed for performing capsulorhexis, such as laser-assisted capsulorhexis, zepto-rhexis (which utilizes precision nano-pulse technology), and marker-assisted capsulorhexis (in which the cornea is marked using a predefined marker, in order to indicate the desired size for the capsule opening).

Subsequently, it is common for a fluid wave to be injected via the corneal incision, in order to dissect the cataract's outer cortical layer, in a step known as hydrodissection. In a subsequent step, known as hydrodelineation, the outer softer epi-nucleus of the lens is separated from the inner firmer endo-nucleus by the injection of a fluid wave. In the next step, ultrasonic emulsification of the lens is performed, in a process known as phacoemulsification. The nucleus of the lens is broken initially using a chopper, following which the outer fragments of the lens are broken and removed, typically using an ultrasonic phacoemulsification probe. Further typically, a separate tool is used to perform suction during the phacoemulsification. When the phacoemulsification is complete, the remaining lens cortex (i.e., the outer layer of the lens) material is aspirated from the capsule. During the phacoemulsification and the aspiration, aspirated fluids are typically replaced with irrigation of a balanced salt solution, in order to maintain fluid pressure in the anterior chamber. In some cases, if deemed to be necessary, then the capsule is polished. Subsequently, the intraocular lens (IOL) is inserted into the capsule. The IOL is typically foldable and is inserted in a folded configuration, before unfolding inside the capsule. At this stage, the viscoelastic is removed, typically using the suction device that was previously used to aspirate fluids from the capsule. If necessary, the incision(s) is sealed by elevating the pressure inside the bulbus oculi (i.e., the globe of the eye), causing the internal tissue to be pressed against the external tissue of the incision, such as to force closed the incision.

SUMMARY

In accordance with some applications of the present invention, a robotic system is configured for use in a microsurgical procedure, such as intraocular surgery. Typically, when used for intraocular surgery, the robotic system includes first and second robotic units. For some applications, each of the robotic units includes an end effector, which is typically configured to securely hold any one of a plurality of different tools thereupon. For some applications, the end effector is coupled to a tool mount, which is configured to hold the tools (directly or indirectly). Typically, the end effector is configured to insert the tool into the patient's eye such that entry of the tool into the patient's eye is via an incision point, and the tip of the tool is disposed within the patient's eye.

For some applications, two multi-jointed arms (i.e., arms containing a plurality of links which are connected to each other via joints) are disposed on a single side of end effector and are configured to moveably support the end effector. Typically, a plurality of arm-motors are associated with the two multi-jointed arms. For some applications, the robotic unit is configured to rotate a tool about its own axis, such as to compensate for rolling of the end effector with respect to the base of the robotic unit. It is typically desirable to prevent a tool (and in particular a tool that is not rotationally symmetrical) from rolling with respect to a patient's eye. For some applications, rather than preventing the end effector from rotating with respect to the base of the robotic unit, the end effector is permitted to roll with respect to the base, but such rolling of the end effector is compensated for by rolling the tool about its own axis with respect to the end effector. For some applications, the robotic unit is configured to rotate a tool about its own axis, for an alternative or additional reason, e.g., in order to perform a surgical maneuver.

Typically, the robotic unit is actively driven to move the end effector along the x-, y-, and z-axes, as well as through pitch and yaw angular movements, whereas rolling of the end effector is an unwanted by-product of such movements. For some applications, a computer processor calculates the amount of roll that the tool should undergo with respect to the end effector. For example, the computer processor may calculate that owing to movement of the multi-jointed arms (e.g., translational movement along the x-, y-, and/or z-axes, and/or pitch and/or yaw angular movement), the end effector will undergo roll of +20 degrees with respect to base. In response thereto, the computer processor may drive the tool to rotate about its own axis with respect to end effector by −20 degrees.

For some applications, as an alternative to or in addition to rolling the tool with respect to the end effector, the end effector itself is rolled. Typically, in such cases, the end effector is rolled about an axis that is not coaxial with the longitudinal axis of the tool. Thus, the end effector undergoes rolling about an axis that is eccentric with respect to its longitudinal axis. For some applications, the robotic unit includes an end-effector motor, which is configured to roll the end effector about the eccentric axis. Typically, the robotic unit includes at least five arm motors. For some applications, the computer processor drives the arms to move such as to compensate for the axis about which the end effector is rolled not being coaxial with the tool axis. In this manner, although the end effector is rotated about the eccentric axis, the tool itself is rolled about its own axis.

For some such applications, each of the multi-jointed arms includes a rotatable arched link in a vicinity of end effector. The rotatable arched link is configured to rotate such as to accommodate rolling of the end effector about axis. Typically, as the end effector is rotated, the end effector pushes the arched link causing it to rotate, such that the end effector becomes accommodated by concavely curved surfaces of the arched links. Such accommodation of the rolling of the end effector is typically desirable, particularly in view of the robotic unit being configured such that the rolling of the end effector is eccentric with respect to its own axis. For example, if in place of the rotatable arched link there was a straight link disposed perpendicularly with respect to end effector axis, then the end effector could only be rotated through a relatively small range of angle before being blocked by the link. By contrast, using a configuration as described herein, the end effector is typically able to roll through more than 180 degrees, e.g., more than 250 degrees, or more than 300 degrees, about the eccentric axis.

For some applications, a sterile drape is provided between (a) the robotic arms and the end effector, which are disposed within a non-sterile zone on a first side of the sterile drape and (b) the tool mount and the tool which are disposed within a sterile zone on a second side of the sterile drape. Typically, the sterile drape is disposed around and sealed with respect to a drape plate. For some applications, the drape plate is couplable to the end effector, and is coupled to (or couplable to) the tool mount. The drape plate typically acts as an interface between (a) the robotic arms and the end effector, which are disposed within a non-sterile zone on a first side of the sterile drape and (b) the tool mount and the tool which are disposed within a sterile zone on a second side of the sterile drape.

For some applications, a tool motor is disposed on the end effector, within the non-sterile zone. The tool motor typically directly drives a motion-transmission portion (such as a pin or a shaft) to move (e.g., to rotate). The motion-transmission portion is configured to transmit motion of the motor to a first gear (e.g., a spur gear (i.e., a gear wheel) or a worm gear) and the first gear drives the tool to rotate with respect to the end effector by driving a second gear (which is typically a spur gear (i.e., a gear wheel) to rotate. (In accordance with respective applications, the second gear is built into the tool itself or can be built into or coupled to the tool sleeve.) Typically, the motion-transmission portion is mechanically coupled to the first gear in such a manner that the interface between the motion-transmission portion and the first gear wheel is sealed (e.g., via an O-ring). Thus, rotational motion of the tool with respect to the end effector is generated by the motor, which is disposed within the non-sterile zone. The rotational motion that is generated by the motor is transmitted to the tool via an interface that maintains the seal between the non-sterile and sterile zones.

For some applications, a linear tool motor is disposed within the non-sterile zone. The linear tool motor typically drives a tool-actuation arm to move linearly. The tool-actuation arm is typically disposed within the non-sterile zone and is configured to push a portion of a tool (such as a plunger of a syringe) linearly by pushing the portion of the tool through the sterile drape. For some applications, a portion of the sterile drape that is disposed at the interface between the tool-actuation arm and the portion of the tool that is pushed is configured to have greater rigidity and/or wearability than other portions of the drape. For example, a sticker may be placed at the portion in order to enhance the rigidity and/or wearability of the portion relative to other portions of the sterile drape. Or, the drape may be treated (e.g., using a heat treatment, or a chemical treatment) at the portion in order to enhance the rigidity and/or wearability of the portion relative to other portions of the sterile drape. Thus, linear motion of a portion of a tool is generated by the linear tool motor, which is disposed within the non-sterile zone. The linear motion that is generated by the motor is transmitted to the portion of the tool via the drape, such as to maintain the seal between the non-sterile and sterile zones.

There is therefore provided, in accordance with some applications of the present invention, apparatus for performing a procedure on a portion of a body of a patient using a tool, the apparatus including:
  a robotic unit including:
    a base;
    an end-effector;
    a tool mount configured to hold the tool;
    a plurality of multi-jointed arms via which the end effector is coupled to the base, each of the multi-jointed arms including a rotatable arched link in a vicinity of the end effector, the rotatable arched link being configured to accommodate rolling of the end effector about an axis that is not coaxial with a longitudinal axis of the tool.

In some applications, the apparatus further includes one or more arm motors configured to move the multi-jointed arms, and a computer processor that is configured to:
  calculate any rolling of the end effector with respect to the base about the axis that is not coaxial with the longitudinal axis of the tool, as a result of movement of the multi-jointed arms; and
  drive the one or more arm motors to move the multi-jointed arms such as to compensate for rolling of the end effector about the axis that is not coaxial with the longitudinal axis of the end effector and the tool, such that the tool rolls about its own longitudinal axis.

In some applications, each of the rotatable arched links defines a concavely curved surface, and the rotatable arched links are configured to accommodate rolling of the end effector by rotating such that the end effector becomes accommodated by the concavely curved surfaces of the rotatable arched links.

In some applications, the apparatus further includes an end effector motor configured to directly roll the end effector with respect to the base, the rotatable arched link is configured to be rotated in a passive manner such as to accommodate the end effector being actively rolled by the end-effector motor.

In some applications, the apparatus further includes a sterile drape and a drape plate, the drape plate is configured to be coupled to the end effector such that the multi-jointed arms and the end effector are disposed in a non-sterile zone on a first side of the sterile drape and the tool mount is disposed within a sterile zone on a second side of the sterile drape.

In some applications, the drape plate is configured to be coupled to the end effector such that all motion-driving portions of the robotic unit that are configured to drive the end effector to move are disposed in the non-sterile zone on the first side of the sterile drape.

In some applications, the rotatable arched link is configured to be rotated such as to accommodate the end effector being rolled through an angle of more than 180 degrees.

In some applications, the rotatable arched link is configured to be rotated such as to accommodate the end effector being rolled through an angle of more than 300 degrees.

In some applications, each of the plurality of multi-jointed arms further includes a first straight link adjacent to a first end of the rotatable arched link and a second straight link adjacent to a second end of the rotatable arched link via which the end effector is coupled to the rotatable arched link, and the second straight link is disposed at an angle with respect to the first straight link.

In some applications, the apparatus further includes a motor within at least one of the arms that is configured to roll the rotatable arched link with respect to the first straight link, the angle between the first straight link and the second straight link is configured such as to cause the rolling of the rotatable arched link with respect to the straight link to result in rolling of the end effector.

There is further provided, in accordance with some applications of the present invention, apparatus for performing a procedure on a portion of a body of a patient using a robotic unit that includes an end-effector and a base, a tool mount that is configured to hold a tool, a tool motor configured to roll the tool with respect to the end effector, and one or more robotic arms that are configured to move the end effector with respect to the base, the apparatus including:
  a drape plate configured to be placed between the tool mount and the end effector;
  a sterile drape disposed around and sealed with respect to the drape plate, and configured to form an interface between a non-sterile zone on a first side of the sterile drape and a sterile zone on a second side of the sterile drape, such that the tool mount is disposed within the sterile zone, and the one or more robotic arms and the tool motor are disposed within the non-sterile zone;
  at least one gear mechanism configured to be disposed within the sterile zone and configured to drive the tool to roll with respect to the end effector; and
  a motion-transmission portion configured to transmit motion from the tool motor to the at least one gear mechanism, while maintaining a seal between the sterile zone and the non-sterile zone.

In some applications, the apparatus further includes at least one computer processor configured to:
  drive the end effector to move with respect to the base by moving the one or more arms,
  calculate any resultant rolling of the end effector with respect to the base, and
  drive the tool motor to roll the tool with respect to the end effector, such as to compensate for any resultant rolling of the end effector with respect to the base.

In some applications, the motion-transmission portion includes a shaft and the tool motor is configured to drive the shaft to rotate, the at least one gear mechanism includes a first gear wheel that is driven to rotate by the shaft and a second gear wheel that is driven to rotate by the first wheel.

In some applications, an interface between the shaft and the first gear wheel is sealed, such as to maintain a seal between the sterile zone and the non-sterile zone.

In some applications, the first gear wheel is disposed within the drape plate.

In some applications, the second gear wheel is built into the tool.

In some applications, the apparatus further includes a tool sleeve configured to be disposed around the tool, the second gear wheel is built into the tool sleeve.

In some applications, the motion-transmission portion includes a shaft and the tool motor is configured to drive the shaft to rotate, the at least one gear mechanism includes a worm gear that is driven to move linearly by the shaft and a gear wheel that is driven to rotate by linear movement of the first wheel.

In some applications, an interface between the shaft and the worm gear is sealed, such as to maintain a seal between the sterile zone and the non-sterile zone. In some applications, the worm gear is disposed within the drape plate. In some applications, the gear wheel is built into the tool. In some applications, the apparatus further includes a tool sleeve configured to be disposed around the tool, the gear wheel is built into the tool sleeve.

In some applications, the apparatus further includes:
  a linear tool motor configured to drive at least a portion of the tool to move linearly with respect to the end effector,
  a tool-actuation arm configured to be moved linearly by the linear tool motor to thereby move at least the portion of the tool linearly with respect to the end effector,
  the sterile drape is configured to form the interface such that the linear tool motor is disposed within the non-sterile zone and such that tool-actuation arm is disposed within the non-sterile zone.

In some applications, a portion of the sterile drape that is configured to be disposed at an interface between the tool-actuation arm and the portion of the tool that is pushed is configured to have greater rigidity and/or wearability than other portions of the drape.

There is further provided, in accordance with some applications of the present invention, apparatus for performing a procedure on a portion of a body of a patient using a robotic unit that includes an end-effector, a tool mount that is configured to hold a tool such that the tool is coaxial with the end effector, a linear tool motor configured to drive at least a portion of the tool to move linearly with respect to the end effector, and one or more robotic arms that are configured to move the end effector, the apparatus including:
  a drape plate configured to be placed between the tool mount and the end effector;
  a sterile drape disposed around and sealed with respect to the drape plate, and configured to form an interface between a non-sterile zone on a first side of the sterile drape and a sterile zone on a second side of the sterile drape, such that the tool mount is disposed within the sterile zone, and the one or more robotic arms and the linear tool motor are disposed within the non-sterile zone; and a tool-actuation arm configured to be disposed within the non-sterile zone, and configured to be moved linearly by the linear tool motor to thereby move at least the portion of the tool linearly with respect to the end effector, and a portion of the sterile drape that is configured to be disposed at an interface between the tool-actuation arm and the portion of the tool that is pushed is configured to have greater rigidity and/or wearability than other portions of the drape.

In some applications, the apparatus includes a sticker placed at the portion of the sterile drape the sticker being configured to enhance the rigidity and/or wearability of the portion relative to the other portions of the sterile drape.

In some applications, the portion of the sterile drape is heat treated to enhance the rigidity and/or wearability of the portion relative to the other portions of the sterile drape.

In some applications, the portion of the sterile drape is chemically treated to enhance the rigidity and/or wearability of the portion relative to the other portions of the sterile drape.

In some applications, the portion of the sterile drape includes an alternative or additional material from the other portions of the sterile drape to enhance the rigidity and/or wearability of the portion relative to the other portions of the sterile drape.

In some applications, the apparatus further includes an automatic tool-actuation arm folding mechanism that is configured to cause the tool-actuation arm to fold automatically in response to being retracted to a given distance from the tool mount.

There is further provided, in accordance with some applications of the present invention, apparatus for performing a procedure on a portion of a body of a patient using a robotic unit that includes an end-effector, tool mount configured to hold a tool such that the tool is coaxial with the end effector, and a linear tool motor configured to drive at least a portion of the tool to move linearly with respect to the end effector, the apparatus including:

a tool-actuation arm configured to be moved linearly by the linear tool motor, to thereby move at least the portion of the tool linearly with respect to the end effector; and an automatic tool-actuation arm folding mechanism that is configured to cause the tool-actuation arm to fold automatically in response to being retracted to a given distance from the tool mount.

In some applications, the automatic tool-actuation arm folding mechanism includes a spring mechanism.

In some applications, the tool includes a syringe that includes a plunger, and the tool-actuation arm is configured to push the plunger of the syringe linearly.

In some applications, the tool-actuation arm is configured to fold such that the tool mount is able to accommodate a large tool without requiring removal and/or manual folding of the tool-actuation arm.

In some applications, the robotic unit is configured for performing cataract surgery using a plurality of tools that include a phacoemulsification probe, and the tool-actuation arm is configured to fold such that the tool mount is able to accommodate the phacoemulsification probe without requiring removal and/or manual folding of the tool-actuation arm.

In some applications, the apparatus further includes an automatic tool-actuation arm unfolding mechanism configured to cause the tool-actuation arm to automatically unfold in response to the tool-actuation arm being moved closer to the tool mount.

In some applications, the automatic tool-actuation arm unfolding mechanism includes a spring mechanism.

There is further provided, in accordance with some applications of the present invention, apparatus for performing a procedure on an eye of a patient using a tool, the apparatus including:

a robotic unit including:
    a base;
    an end-effector;
    a tool mount configured to hold the tool;
    a plurality of multi-jointed arms via which the end effector is coupled to the base, the multi-jointed arms being configured to permit movement of the end effector with respect to the base that is such that the end effector rolls with respect to the base;
    at least one arm motor configured to move the multi-jointed arms; and
    at least one tool motor configured to rotate the tool with respect to the end effector, about a longitudinal axis of the tool; and at least one computer processor configured to:
    drive the arm motor to move the end effector with respect to the base by moving the multi-jointed arms,
    calculate any resultant rolling of the end effector with respect to the base, and
    drive the tool motor to roll the tool about its own longitudinal axis, such as to compensate for any resultant rolling of the end effector with respect to the base.

In some applications, the robotic unit is configured to perform at least a portion of a cataract procedure on the patient's eye.

The present invention will be more fully understood from the following detailed description of applications thereof, taken together with the drawings, in which:

BRIEF DESCRIPTION OF THE DRAWINGS

FIG. 8 is a schematic illustration of a sterile drape and drape plate for use with a robotic unit that is not configured to rotate a tool within the end effector, in accordance with some applications of the present invention;

FIGS. 10A, 10B, and 10C are schematic illustrations of a sterile drape and drape plate for use with a robotic unit that is configured to rotate a tool within the end effector, in accordance with some alternative applications of the present invention;

FIG. 13 is a schematic illustration of an end effector that includes an automatically foldable tool-actuation arm, for pushing a tool or a portion thereof linearly, in accordance with some applications of the present invention.

DETAILED DESCRIPTION OF EMBODIMENTS

Figure 1:
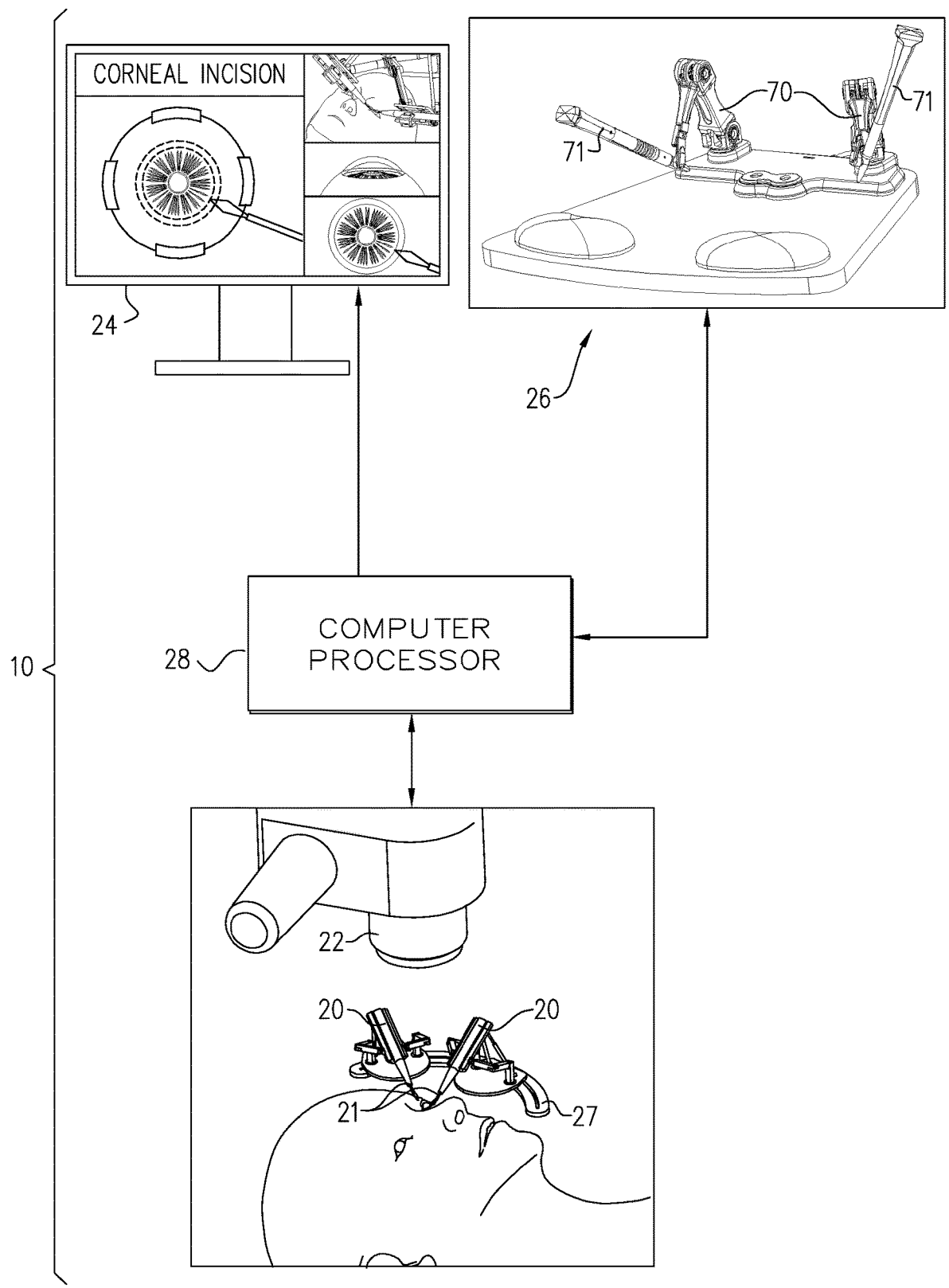
FIG. 1 is a schematic illustration of a robotic system that is configured for use in a microsurgical procedure, such as intraocular surgery, in accordance with some applications of the present invention.

Reference is now made to FIG. 1, which is a schematic illustration of a robotic system 10 that is configured for use in a microsurgical procedure, such as intraocular surgery, in accordance with some applications of the present invention. Typically, when used for intraocular surgery, robotic system 10 includes first and second robotic units 20 (which are configured to hold tools 21), in addition to an imaging system 22, a display 24 and a control component 26 (e.g., a pair of control devices, such as joysticks, as shown), via which a user (e.g., a healthcare professional) is able to control robotic units 20. Typically, robotic system 10 includes one or more computer processors 28, via which components of the system and a user (e.g., a healthcare professional) operatively interact with each other. For some applications, each of first and second robotic units is supported on a base 27, as shown. The scope of the present application includes mounting first and second robotic units in any of a variety of different positions with respect to each other.

Typically, movement of the robotic units (and/or control of other aspects of the robotic system) is at least partially controlled by a user (e.g., a healthcare professional). For example, the user may receive images of the patient's eye and the robotic units, and/or tools disposed therein, via display 24. Typically, such images are acquired by imaging system 22. For some applications, imaging system 22 is a stereoscopic imaging device and display 24 is a stereoscopic display. Based on the received images, the user typically performs steps of the procedure. For some applications, the user provides commands to the robotic units via control component 26. Typically, such commands include commands that control the position and/or orientation of tools that are disposed within the robotic units, and/or commands that control actions that are performed by the tools. For example, the commands may control a phacoemulsification tool (e.g., the operation mode and/or suction power of the phacoemulsification tool), and/or injector tools (e.g., which fluid (e.g., viscoelastic fluid, saline, etc.) should be injected, and/or at what flow rate). Alternatively or additionally, the user may input commands that control the imaging system (e.g., the zoom, focus, and/or x-y positioning of the imaging system). For some applications, the commands include controlling an IOL-manipulator tool, for example, such that the tool manipulates the IOL inside the eye for precise positioning of the IOL within the eye.

Figure 2A:
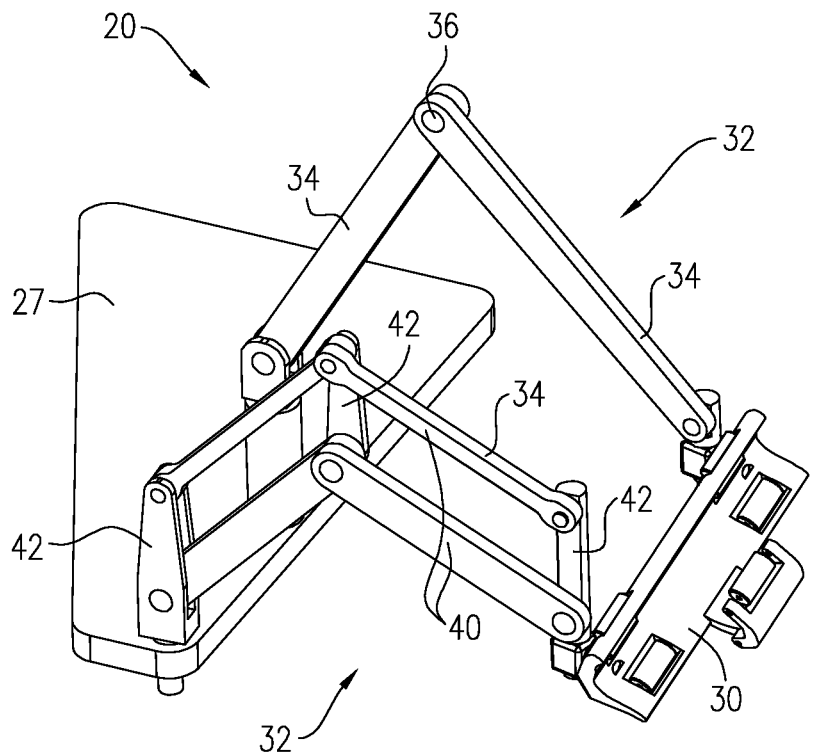
FIGS. 2A and 2B are schematic illustrations of a robotic unit for use in a robotic system, in accordance with some applications of the present invention.
Figure 2B:
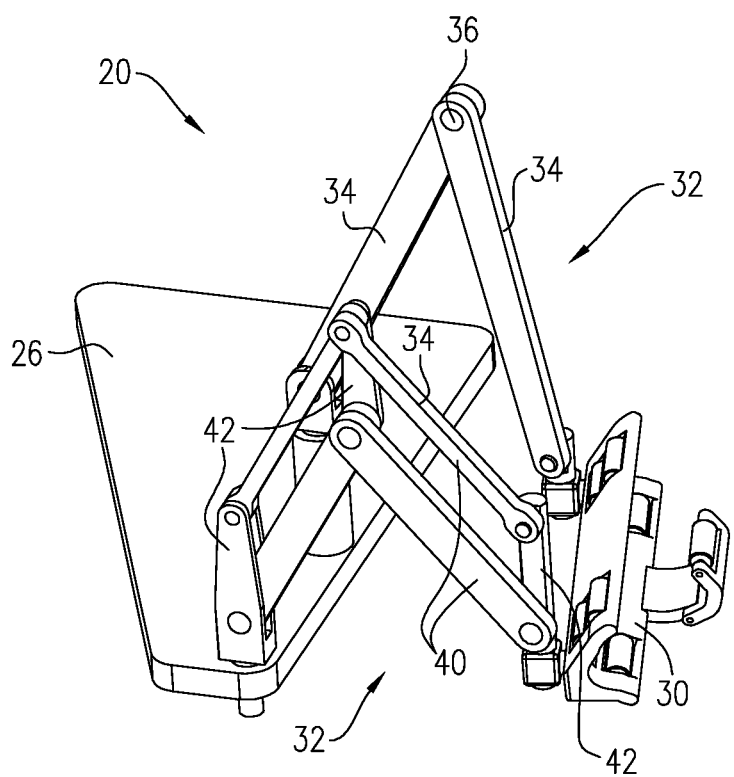

Reference is now made to FIGS. 2A and 2B, which are schematic illustrations of robotic unit 20 for use in robotic system 10, in accordance with some applications of the present invention. For some applications, each of the robotic units includes an end effector 30. The end effector is typically configured to securely hold any one of a plurality of different tools 21 (shown in FIG. 1) thereupon. For some applications, the end effector is coupled to a tool mount, which is configured to hold the tools (directly or indirectly), e.g., as described in further detail hereinbelow. Typically, the end effector is configured to insert the tool into the patient's eye such that entry of the tool into the patient's eye is via an incision point, and the tip of the tool is disposed within the patient's eye.

For some applications, two multi-jointed arms 32 (i.e., arms containing a plurality of links 34 which are connected to each other via joints 36) are disposed on a single side of end effector 30 and are configured to moveably support the end effector. Typically, the computer processor detects movement of the patient's eye in three dimensions, by analyzing images acquired by imaging system 22 (which as described hereinabove is typically a stereoscopic imaging system). For some applications, in response to the detected movement of the patient's eye, the computer processor drives the robotic unit to move the tool such that entry of the tool into the patient's eye remains via the incision point even as the patient's eye undergoes the movement in three dimensions. Typically, even as the patient's eye undergoes the movement in three dimensions, the computer processor drives the robotic unit to perform at least a portion of a procedure on the patient's eye by moving the tip of the tool in a desired manner with respect to the eye such as to perform the portion of the procedure, while entry of the tool into the patient's eye is maintained fixed at incision point. In this manner, the robotic unit acts to provide a dynamic remote center of motion that is located at the incision point, and about which motion of the tool is centered. Typically, the remote center of motion moves in coordination with movement of the eye. Alternatively or additionally, the computer processor is configured to detect when the eye is at a given position, and to time the performance of certain functions by the robotic units such that they are performed when the eye is at the given position.

Typically, a plurality of arm-motors are associated with the two multi-jointed arms 32. Although not shown in FIGS. 2A and 2B, the locations of arm motors are shown in FIGS. 3B, 4C, and 6B. For some applications, the plurality of arm-motors move the end effector through five degrees-of-freedom (e.g., translational movement along the x-, y-, and z-axes, as well as pitch and yaw angular movement). It may be observed that in the example shown in FIGS. 2A-B, each link 34 of at least one of the multi-jointed arms 32 of the robotic system includes two parallel bars 40 that extend between vertical joints 42, with a vertical joint disposed between each pair of adjacent links. For some applications, the arrangement of parallel bars and vertical joints results in the ends of each of the joints of a given multi-jointed arm remaining parallel with each other, even as the arm moves (as shown in the transition from FIG. 2A to FIG. 2B). In turn, this prevents the end effector from being rolled with respect to base 27. Put another way, the arrangement of parallel bars and vertical joints results in roll of the end effector being mechanically decoupled from translational movement and pitch-yaw angular movement of the end effector. For some applications, preventing the end effector from being rolled with respect to base 27 is desirable in order to prevent tool 21 from rolling with respect to the patient's eye. In particular, for tools that are not rotationally symmetrical it may be desirable to prevent the tools from rolling with respect to the patient's eye. For some applications, each of the multi-jointed arms is configured in the above-described manner. Alternatively, only one of the multi-jointed arms is configured in the above-described manner.

Figure 3A:
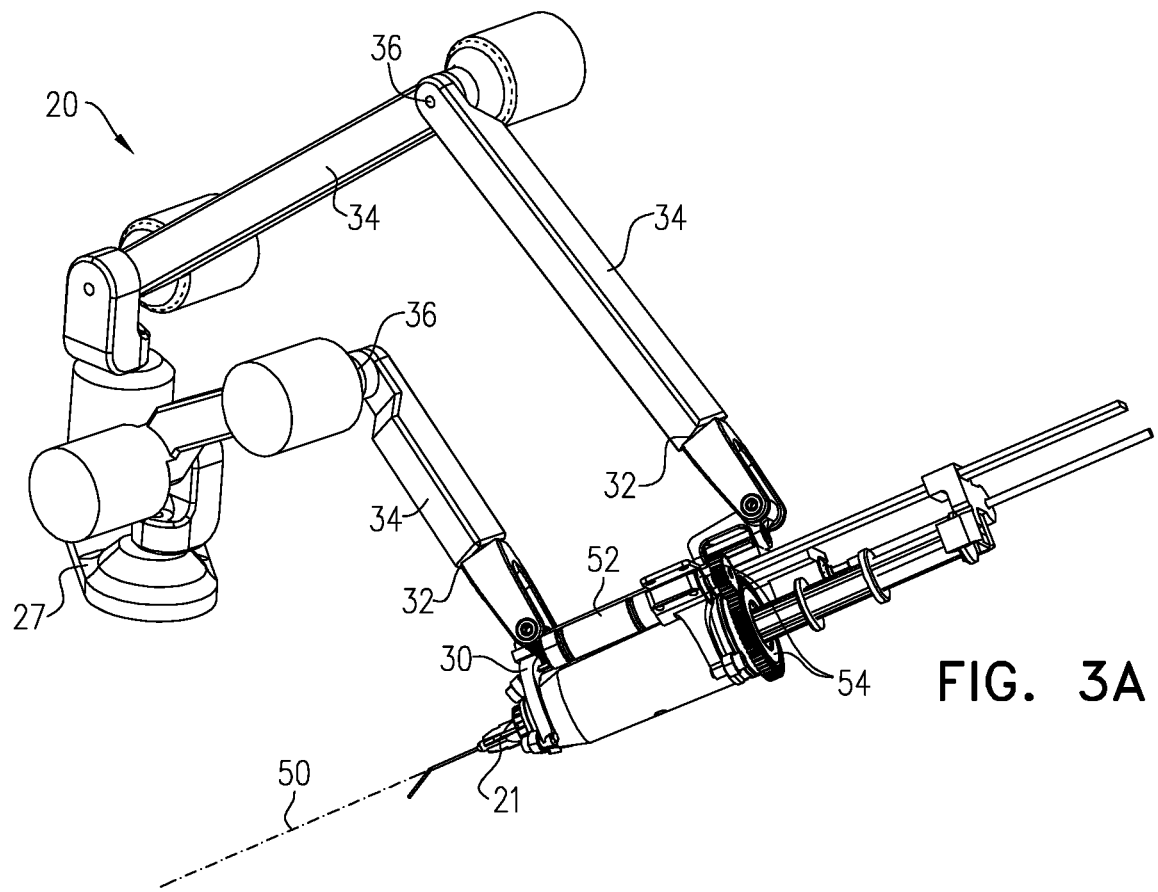
FIGS. 3A and 3B are schematic illustrations of a robotic unit that is configured to roll a tool about its own axis, such as to compensate for rolling of an end effector of the robotic unit with respect to a base of the robotic unit, in accordance with some applications of the present invention.
Figure 3B:
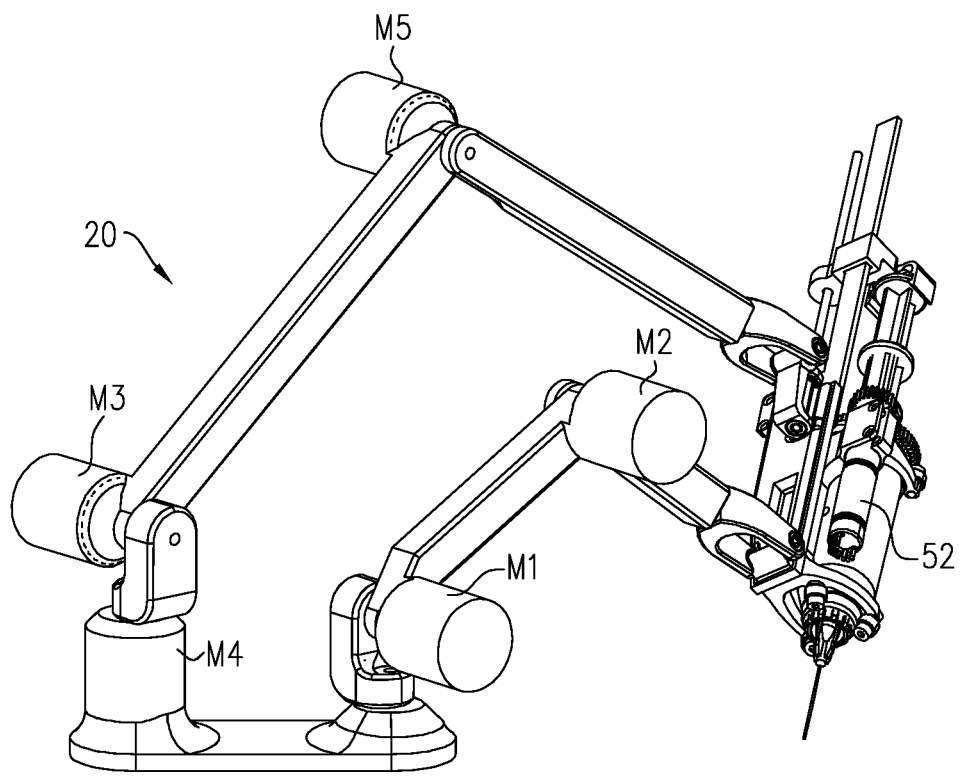

Reference is now made to FIGS. 3A and 3B, which are schematic illustrations of robotic unit 20 that is configured to rotate tool 21 about its own axis, such as to compensate for rolling of end effector 30 of the robotic unit with respect to base 27 of the robotic unit, in accordance with some alternative applications of the present invention. (In FIG. 3B, many of the reference numerals are not included, in order to focus specifically on the typical positions of the arm motors within the robotic unit.) As noted above, it is typically desirable to prevent a tool (and in particular a tool that is not rotationally symmetrical) from rolling with respect to the patient's eye. In the case of procedures (such as cataract procedures) that are performed on the eye, many of the tools are not rotationally symmetrical and the dimensions of the surgical space are relatively small. For some applications, rather than preventing the end effector from rotating with respect to base 27 (e.g., as described with reference to FIGS. 2A and 2B), the end effector is permitted to roll with respect to the base, but such rolling of the end effector is compensated for by rolling the tool about its own axis 50 with respect to the end effector. For some applications, the robotic unit is configured to rotate a tool about its own axis, for an alternative or additional reason, e.g., in order to perform a surgical maneuver.

For example, as shown in FIGS. 3A and 3B, neither one of multi-jointed arms 32 includes an arrangement of parallel bars, as described hereinabove with reference to FIGS. 2A-B. Thus, the robotic unit is configured to move the end effector through six degrees-of-freedom (e.g., translational movement along the x-, y-, and z-axes, as well as pitch, yaw, and roll angular movement). Typically, the robotic unit is actively driven to move the end effector along the x-, y-, and z-axes, as well as through pitch and yaw angular movements, whereas the rolling of the end effector is an unwanted by-product of such movements. Further typically, the robotic unit includes at least five arm motors M1-M5, as shown in FIG. 3B.

For some applications, computer processor 28 (shown in FIG. 1) calculates the amount of roll that the tool should undergo with respect to the end effector. For example, computer processor 28 may calculate that owing to movement of the multi-jointed arms (e.g., translational movement along the x-, y-, and/or z-axes, and/or pitch and/or yaw angular movement), the end effector will undergo roll of +20 degrees with respect to base. In response thereto, the computer processor may drive the tool to rotate about its own axis 50 with respect to end effector by −20 degrees. The tool is typically held by the end effector (or by a tool mount) such that the tool is coaxial with the end effector (or is coaxial with the tool mount). Therefore, longitudinal axis 50 of the tool is typically also the longitudinal axis of the end effector (or of the tool mount). Thus, in the example shown in FIGS. 3A and 3B, longitudinal axis 50, around which the tool is rotated, is coaxial with the end effector longitudinal axis.

As shown in FIGS. 3A and 3B, for some such applications, a tool motor 52 is configured to roll the tool with respect to the end effector. For some applications, the tool motor drives the tool to roll with respect to the end effector, via an arrangement of gear wheels 54, as shown.

Figure 4A:
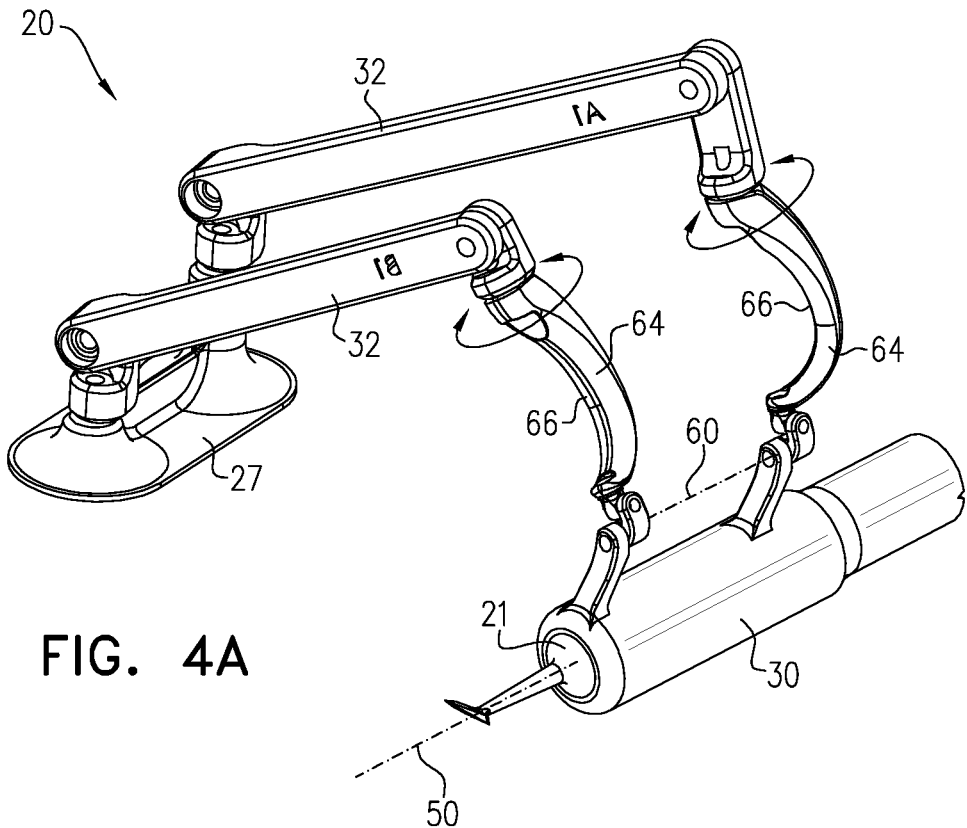
FIGS. 4A, 4B, and 4C are schematic illustrations of a robotic unit having an end effector that is configured to be rolled about an axis, in accordance with some alternative applications of the present invention.
Figure 4B:
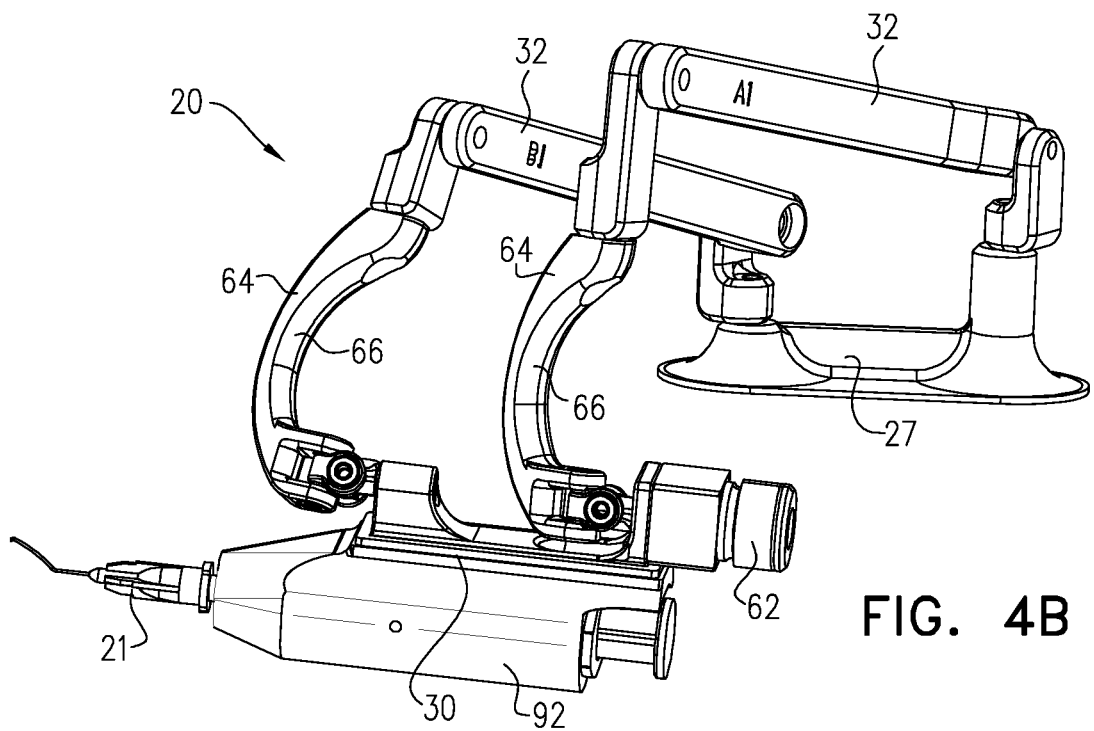
Figure 4C:
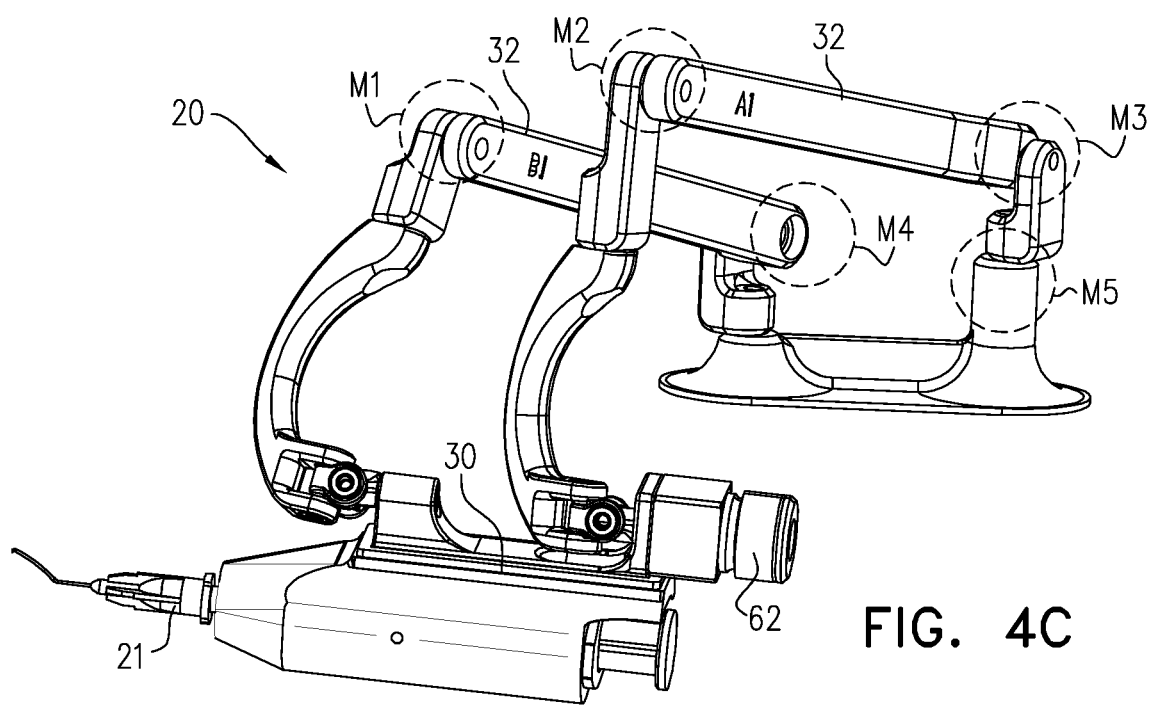
Figure 5C:
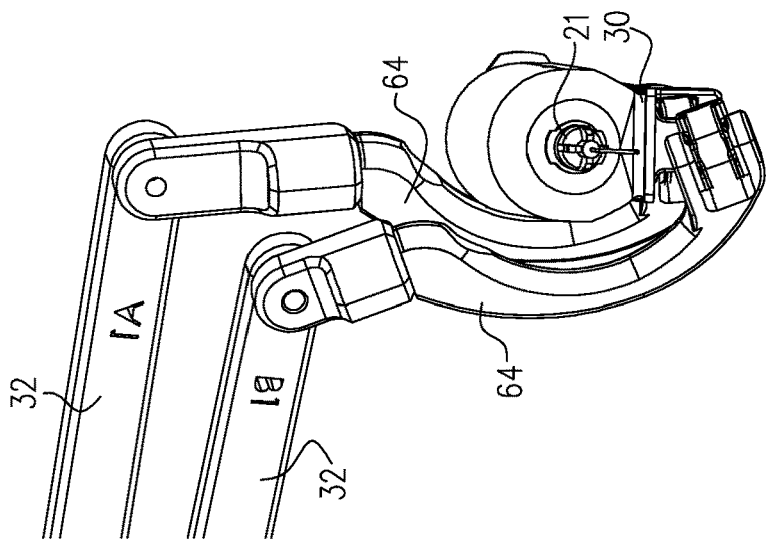
FIGS. 5A, 5B, and 5C are schematic illustrations of the robotic unit of FIGS. 4A and 4B at respective stages of a rolling motion of the end effector of the robotic unit, in accordance with some alternative applications of the present invention.
Figure 5B:
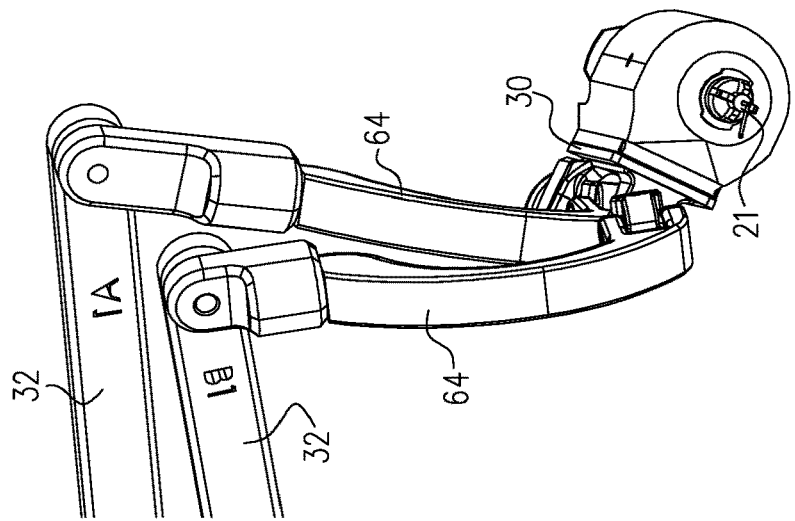
Figure 5A:
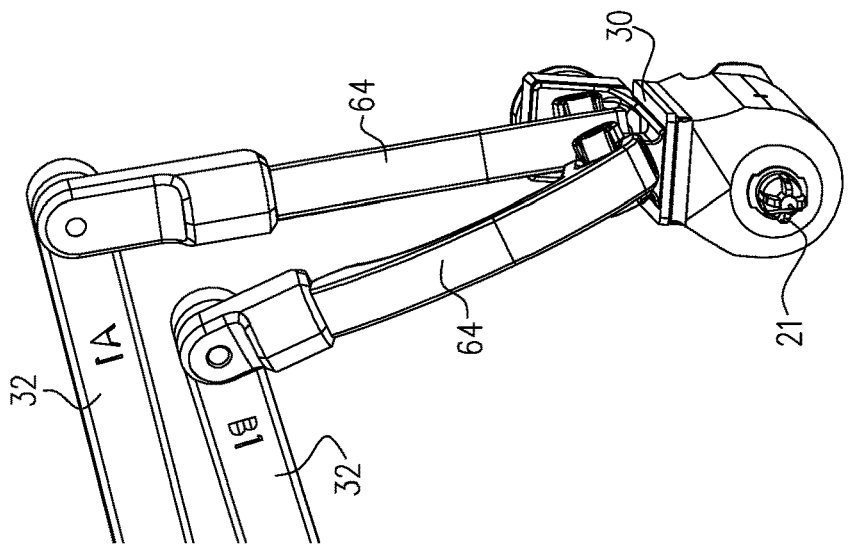

Reference is now made to FIGS. 4A, 4B, and 4C which are schematic illustrations of robotic unit 20, end effector 30 of the robotic unit being configured to be rolled about an axis 60 that is not coaxial with its own longitudinal axis 50, in accordance with some applications of the present invention. For some applications, the end effector is coupled with (or forms an integrated structure with) a tool mount 92, which is configured to hold the tool, as shown in FIG. 4B. FIG. 4C is similar to FIG. 4B, but many of the reference numerals are not included in FIG. 4C, in order to focus specifically on the typical positions of the arm motors within the robotic unit. Reference is also made to FIGS. 5A, 5B, and 5C, which are schematic illustrations of the robotic unit of FIGS. 4A, 4B and 4C at respective stages of a rolling motion of end effector 30, in accordance with some alternative applications of the present invention. It is noted that in some of the figures (e.g., FIGS. 5a-5C), there are symbols on robotic arms 32 (e.g., symbols A1 and B1). These symbols are included in order to demonstrate the orientations of the robotic arms in respective figures.

For some applications, as an alternative to or in addition to rolling the tool with respect to the end effector, the end effector itself is rolled. Typically, in such cases, the end effector is rolled about axis 60, which is not coaxial with axis 50 of tool 21 and of end effector 30. (Thus, the end effector undergoes eccentric rolling with respect to its longitudinal axis.) For some applications, the robotic unit includes an end-effector motor 62, which is configured to roll the end effector about axis 60 (shown in FIG. 4A). Typically, the robotic unit includes at least five arm motors, with the locations of the arm motors being illustrated schematically by the dashed circles labelled M1-M5, in FIG. 4C. For some applications, the computer processor drives the arms to move such as to compensate for axis 60 not being coaxial with the tool axis. In this manner, although the end effector is rotated about axis 60 via end-effector motor 62, the tool itself is rolled about its own axis.

For some such applications, each of multi-jointed arms 32 comprising a rotatable arched link 64 in a vicinity of end effector 30. The rotatable arched link is configured to rotate such as to accommodate rolling of the end effector about axis 60. This may be observed by observing the transition from FIG. 5A to 5B and then from FIG. 5B to FIG. 5C. As shown, as the end effector is rotated, the end effector pushes the arched link causing it to rotate, such that the end effector becomes accommodated by concavely curved surfaces 66 of the arched links. Such accommodation of the rolling of the end effector is typically desirable, particularly in view of the robotic unit being configured such that the rolling of the end effector is eccentric with respect to its own axis. For example, if in place of the rotatable arched link there was a straight link disposed perpendicularly with respect to end effector axis, then the end effector could only be rotated through a relatively small range of angle about axis 60 before being blocked by the link. By contrast, using the configuration shown in FIGS. 4A-5C, the end effector is typically able to roll through more than 180 degrees, e.g., more than 250 degrees, or more than 300 degrees, about axis 60.

Figure 6A:
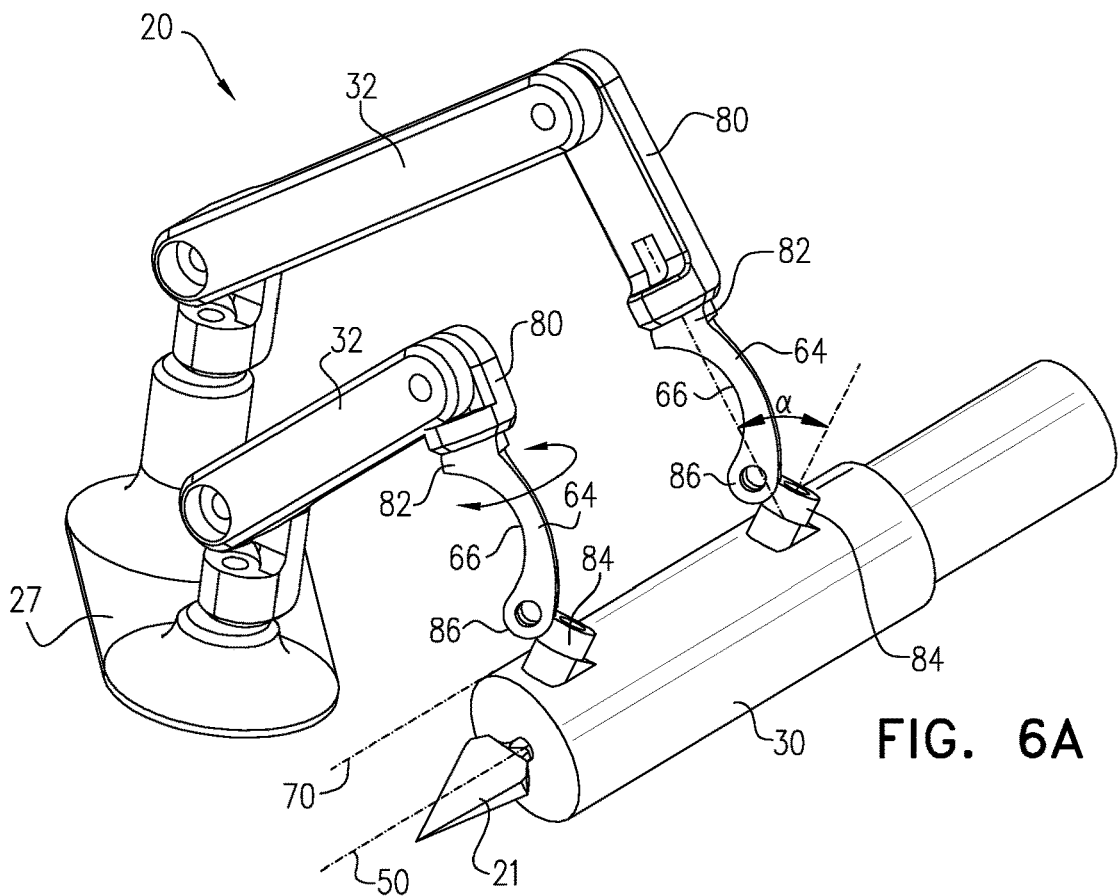
FIGS. 6A and 6B are schematic illustrations of a robotic unit having an end effector that is configured to be rolled about an axis that is not coaxial with its own longitudinal axis, in accordance with some alternative applications of the present invention.
Figure 6B:
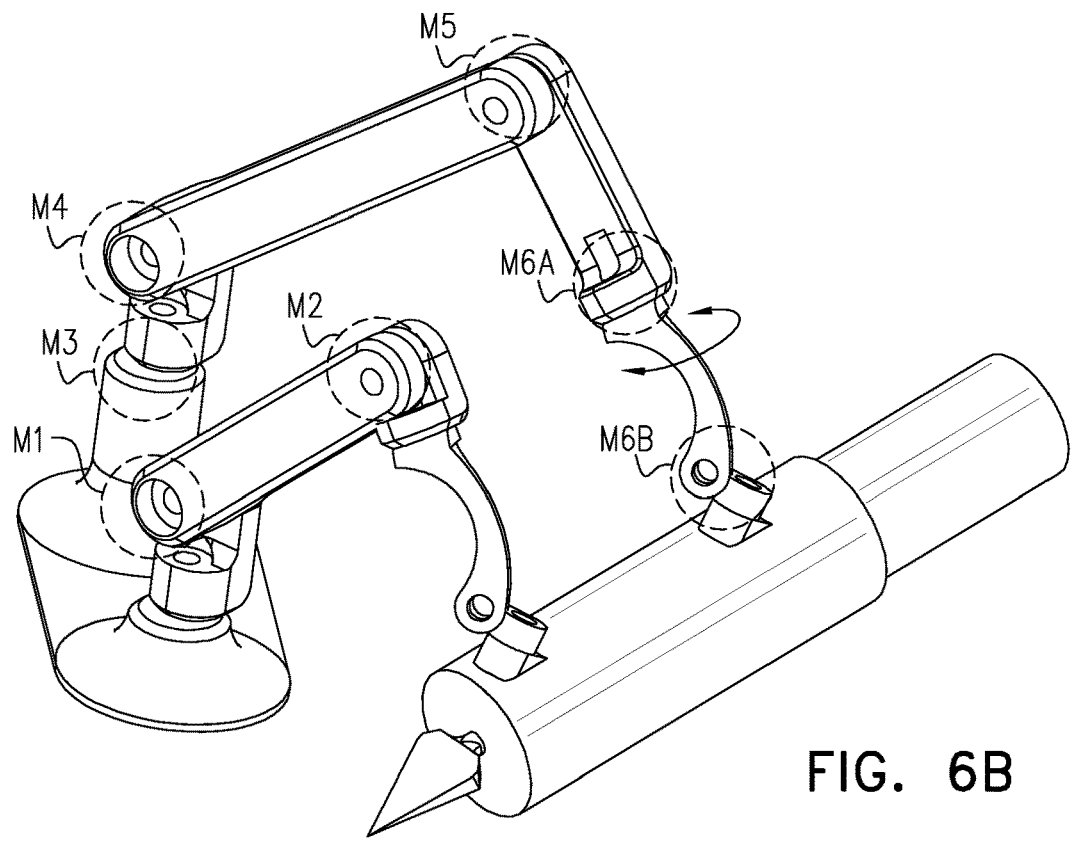
Figure 7C:
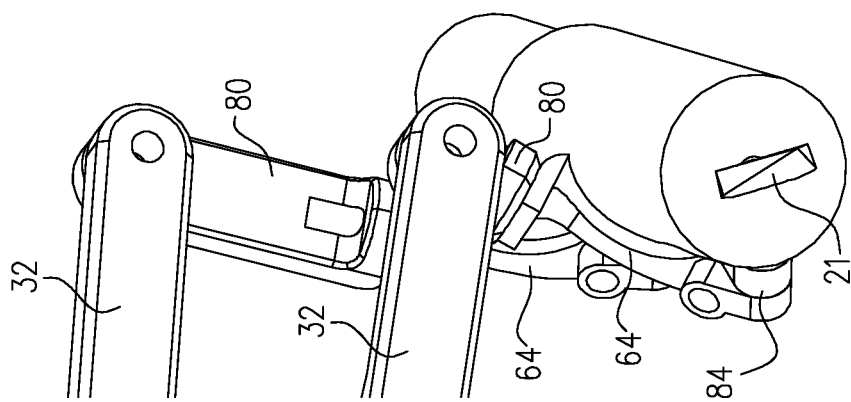
FIGS. 7A, 7B, and 7C are schematic illustrations of the robotic unit of FIGS. 6A and 6B at respective stages of a rolling motion of the end effector of the robotic unit, in accordance with some alternative applications of the present invention.
Figure 7B:
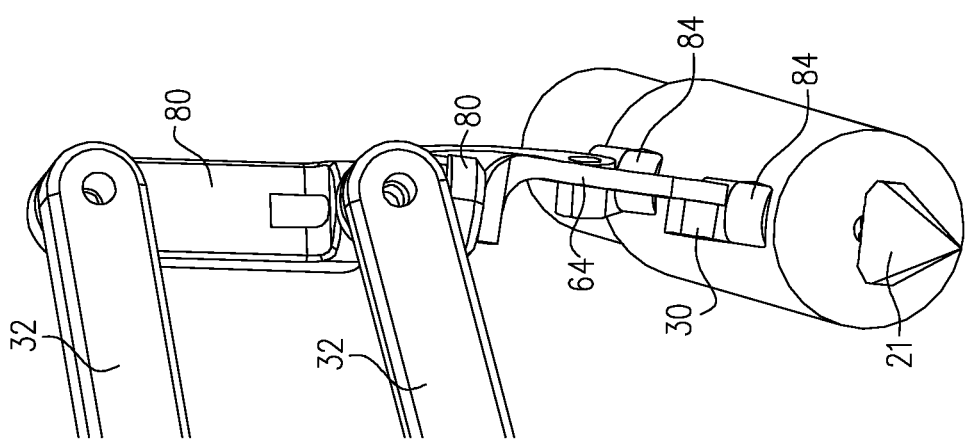
Figure 7A:
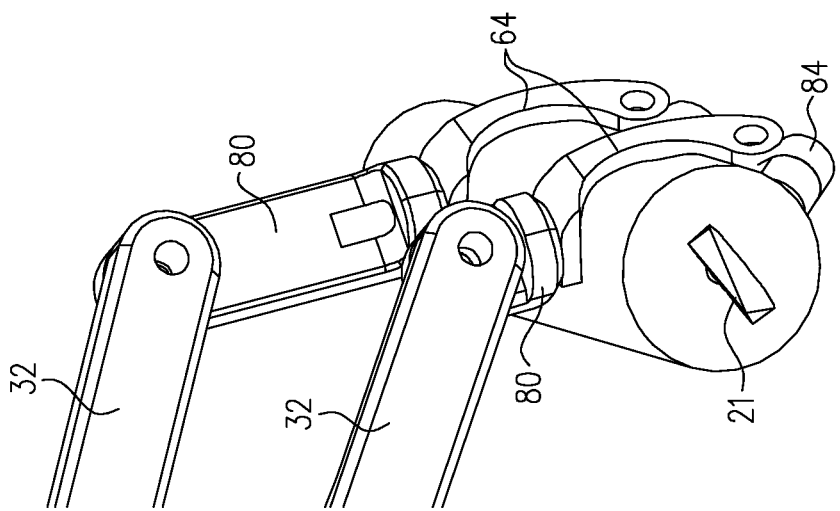

Reference is now made to FIGS. 6A and 6B, which are schematic illustrations of robotic unit 20, end effector 30 of the robotic unit being configured to be rolled about an axis 70 that is not coaxial with its own longitudinal axis 50, in accordance with some applications of the present invention. FIG. 6B is similar to FIG. 6A, but many of the reference numerals are not included in FIG. 6B, in order to focus specifically on the typical positions of the arm motors within the robotic unit. Reference is also made to FIGS. 7A, 7B, and 7C, which are schematic illustrations of the robotic unit of FIG. 6 at respective stages of a rolling motion of end effector 30, in accordance with some alternative applications of the present invention.

As described with reference to FIGS. 4A-5C, for some applications, each of the multi-jointed arms includes rotatable arched link 64 in a vicinity of end effector 30. The rotatable arched link being configured to rotate such as to accommodate rolling of the end effector about axis 70, in a generally similar manner to that described hereinabove. For some such applications, a first straight link 80 is disposed adjacent to a first end 82 of the rotatable arched link and a second straight link 84 is disposed adjacent to a second end 86 of the rotatable arched link (with the end effector being coupled to the rotatable arched link via second straight link 84). As shown in FIG. 6A, for some applications, the second straight link is disposed at an angle alpha with respect to first straight link 80.

Typically, the robotic unit includes at least five arm motors, with the locations of the arm motors being illustrated schematically by the dashed circles labelled M1-M5, in FIG. 6B. For some applications, the robotic unit includes a further motor mounted in a vicinity of straight link 80 or straight link 84 of one of the arms. For example, the robotic unit may include a further motor mounted at either the location that is indicated by the dashed circle that is labelled M6A or at the location that is indicated by the dashed circle that is labelled M6B in FIG. 6B. The further motor is configured to roll rotatable arched link 64 with respect to straight links 80 and 84. Typically, by virtue of the second straight links being disposed at angle alpha with respect to the first straight links, rolling of rotatable arched link 64 with respect to straight link 80 causes the second straight links to swivel with respect to the first straight links. In turn, this causes the end effector to roll about axis 70. This may be observed in the transition from 7A to FIG. 7B and then from FIG. 7B to FIG. 7C. Typically, for such applications, computer processor 28 calculates how to move links of the arms such as to cause the end effector to roll about axis 70 in a desired manner. As described with reference to FIGS. 4A-5C, as the end effector is rotated, the end effector becomes accommodated by concavely curved surfaces 66 of the arched links. Typically, using the configuration shown in FIGS. 6A-7C, the end effector is able to roll (eccentrically with respect to its own axis) through more than 180 degrees, e.g., more than 250 degrees, or more than 300 degrees, about axis 70.

Reference is now made to FIG. 8, which is a schematic illustration of a sterile drape 88 and drape plate 90 for use with a robotic unit 20 that is not configured to rotate tool 21 within end effector 30, in accordance with some applications of the present invention. For example, a sterile drape and drape plate as shown in FIG. 8 may be used with robotic units that are as described with reference to FIGS. 4A-C and/or with reference to FIGS. 6A-B, whereby any rotation of the tool is typically effected by rotating the end effector, rather than rotating the tool with respect to the end effector. Typically, in such cases, all of the motion-driving portions of the robotic unit (such as motors, gear wheel, etc.) that are configured to drive the end effector to move, as well as end effector 30 itself, are disposed within a non-sterile zone on a first side of the sterile drape (i.e., on the side of the sterile drape on which the arms of the robotic unit are disposed). A tool mount 92 (which is configured to hold the tool, directly or indirectly) is disposed within a sterile zone on a second side of the sterile drape, and is couplable to the drape plate. Typically, the sterile drape is disposed around and sealed with respect to the drape plate. The drape plate is couplable to (or coupled to) both the end effector and the tool mount. For example, end effector 30, which is disposed within the non-sterile zone at the ends of the arms, may be configured to be coupled to one side of the drape plate, and tool mount may define a portion 94 on its reverse side that is configured to become coupled to a second side of the drape plate. Typically, drape plate 90 acts as an interface between (a) arms 32 and end effector 30, which are disposed within a non-sterile zone on a first side of the sterile drape and (b) tool mount 92 and tool 21, which are disposed within a sterile zone on a second side of the sterile drape. When the drape plate is coupled to both the end effector and to the tool mount, movement of the arms and the end effector (which is generated within the non-sterile zone) is transmitted to tool mount 92 and to tool 21 (both of which are disposed within the sterile zone), via the drape plate. (It is noted that in some cases, the tool itself is disposed within the tool mount. Alternatively, as shown, the tool is disposed inside a tool sleeve 23, which is disposed within tool mount 92.)

Figure 9:
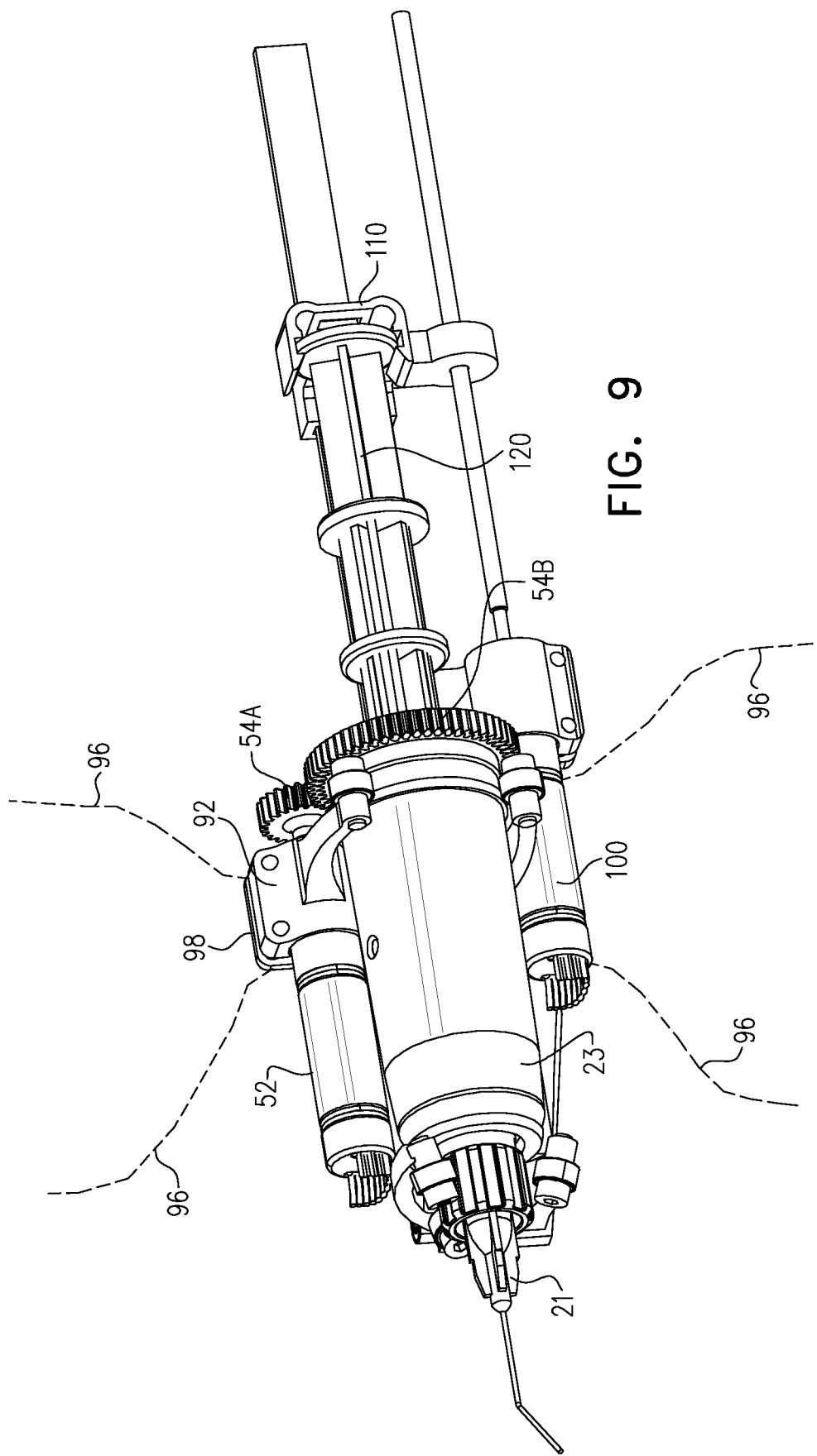
FIG. 9 is a schematic illustration of a sterile drape and drape plate for use with a robotic unit that is configured to rotate a tool within the end effector, in accordance with some applications of the present invention.

Reference is now made to FIG. 9, which is a schematic illustration of a sterile drape 96 and drape plate 98 for use with a robotic unit in which the tool is rotated within the end effector, in accordance with some applications of the present invention. For example, a sterile drape and drape plate as shown in FIG. 9 may be used with a robotic unit as described with reference to FIGS. 3A-B, which show an example of robotic unit 20 that is configured to rotate tool 21 about its own axis. For some such cases, at least some of the motion-driving portions of the robotic unit (such as motors, gear wheel, etc.) that are configured to drive the end effector and/or the tool to move are disposed within the sterile zone (i.e., the side of the drape that is shown in FIG. 9). For some applications, tool motor 52 and/or gear wheels 54A and 54B (which are configured to roll the tool with respect to the end effector) are disposed within the sterile zone. (It is noted that in some cases, the tool itself includes an in-built gear wheel, and is directly rotated by gear wheel MA that is driven to rotate by the motor. Alternatively, as shown, the tool is disposed inside tool sleeve 23 that includes or is coupled to gear wheel MB, which is rotated by gear wheel MA.) For some applications, a linear tool motor 100 that is configured to drive a portion of the tool to move linearly is disposed within the sterile zone. Linear tool motor is typically configured to move a portion of a tool (such as a plunger 120 of a syringe) linearly via a tool actuation arm 110. Some examples of the linear tool motor and tool actuation arm are described in further detail hereinbelow.

Typically, all portions of the apparatus that are configured to be disposed within the sterile zone are configured to be disposable and/or sterilizable (e.g., via autoclaving). For applications as shown in FIG. 9, typically tool motor 52, gear wheel 54A, tool sleeve 23 (and gear wheel 54B), linear tool motor 100, and tool actuation arm 110 are all configured to be disposable and/or sterilizable (typically, via autoclaving). Typically, tool motor 52 and linear tool motor 100 are powered via a sealed electrical connector that passes through the sterile drape and/or by an external cable.

Typically, sterile drape 96 is disposed around and sealed with respect to drape plate 98. For some applications, arms 32 and end effector 30 (arms and end effector not shown in FIG. 9) are disposed within the non-sterile zone, and drape plate 98 is couplable to the end effector. Typically drape plate 98 acts as an interface between (a) end effector 30 and arms 32 (which are not shown in FIG. 9 and) which are disposed within a non-sterile zone on a first side of the sterile drape, and (b) tool mount 92 and tool 21 which are disposed within a sterile zone on a second side of the sterile drape. When the drape plate is coupled to both the end effector and to the tool mount, then movement of the arms and the end effector (which is generated within the non-sterile zone) is transmitted to tool mount 92 and to tool 21 (both of which are disposed within the sterile zone), via drape plate 98. However, as described above, for applications such as that shown in FIG. 9, movement of the tool (or a portion thereof) with respect to the end effector is effected from within the sterile zone, via tool motor 52 and/or linear tool motor 100.

Figure 10A:
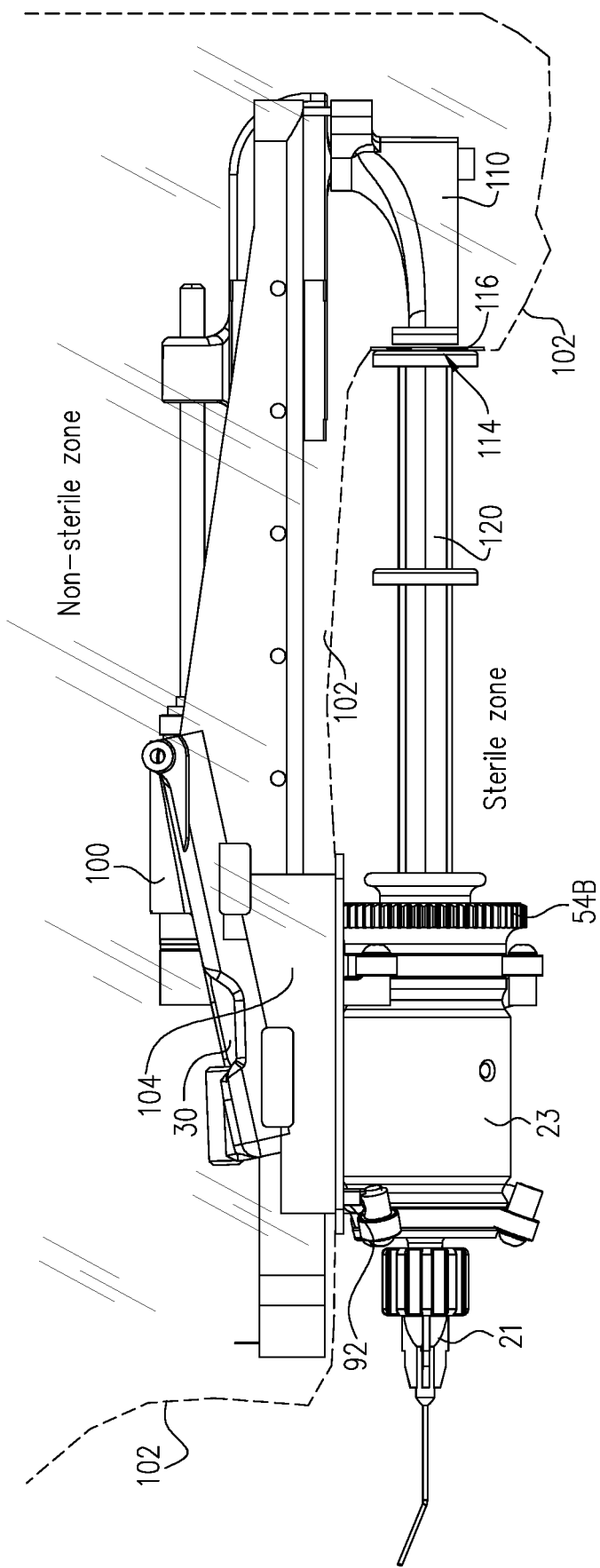
Figure 10B:
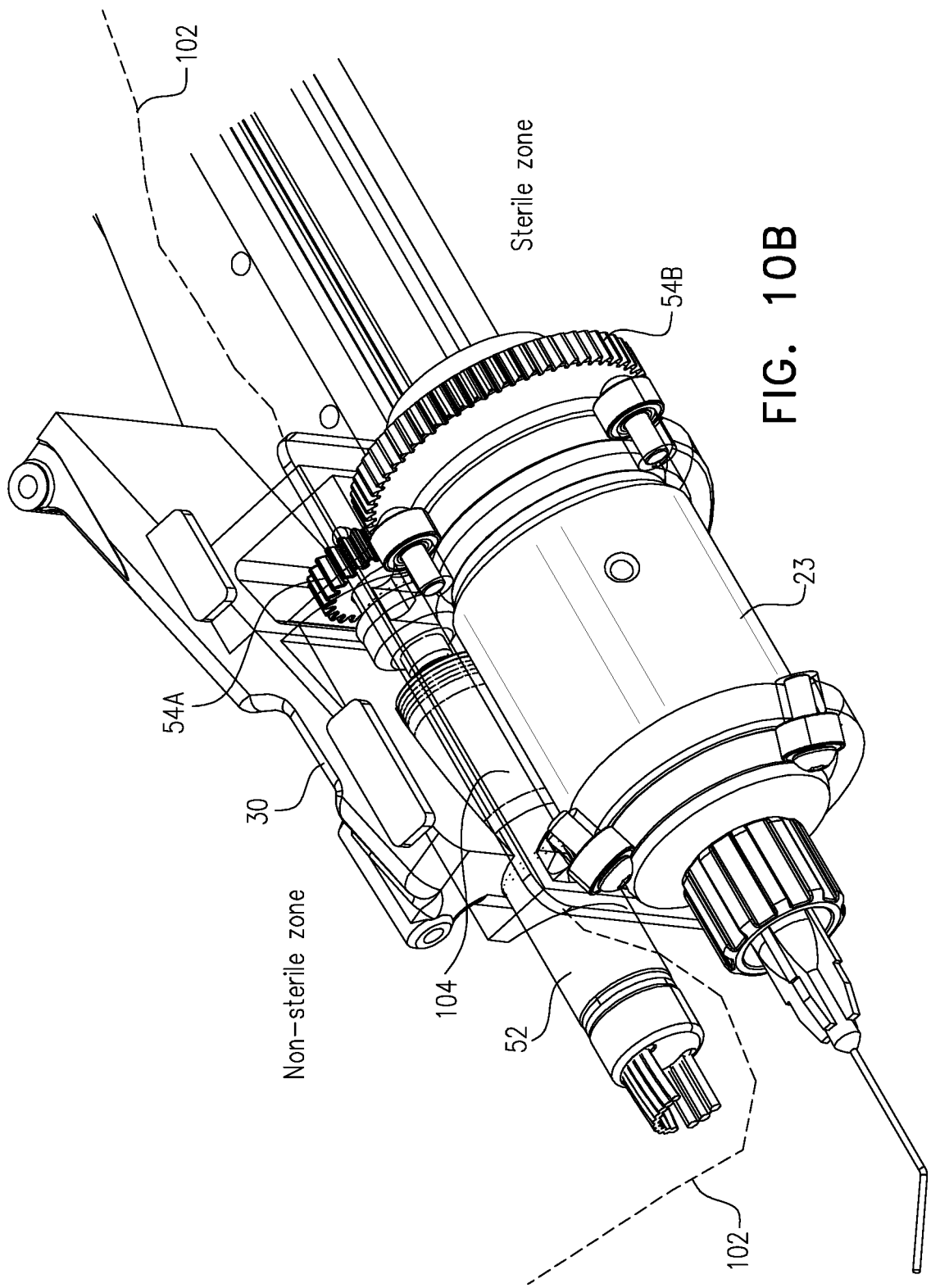

Reference is now made to FIGS. 10A, 10B, and 10C, which are schematic illustrations of a sterile drape 102 and drape plate 104 for use with a robotic unit 20 that is configured to rotate tool 21 within end effector 30, in accordance with some alternative applications of the present invention. Typically drape plate 104 acts as an interface between (a) arms 32 (which are not shown in FIGS. 10A-C and) and end effector 30, which are disposed within a non-sterile zone on a first side of the sterile drape and (b) tool mount 92 and tool 21 which are disposed within a sterile zone on a second side of the sterile drape.

For some applications, tool motor 52 (shown in FIGS. 10B-C) is disposed on end effector 30, within the non-sterile zone. Tool motor 52 typically directly drives a motion-transmission portion 106 (such as a pin or a shaft) to rotate. The motion-transmission portion is configured to transmit rotational motion of the motor to first gear wheel (i.e., spur gear) 54A and the first gear wheel drives the tool to rotate with respect to the end effector by driving second gear wheel (i.e., spur gear) 54B to rotate. For some applications, the first gear wheel is disposed within (e.g., built into) the drape plate. As described hereinabove, second gear wheel 54B can be built into the tool itself or can be built into or coupled to tool sleeve 23. Typically, motion-transmission portion 106 is mechanically coupled to first gear wheel 54A in such a manner that the interface between the motion-transmission portion and first gear wheel 54A is sealed such as to maintain a seal between the sterile zone and the non-sterile zone (e.g., via an O-ring 108, as shown in FIG. 10C). Thus, in the example shown in FIGS. 10A-C, rotational motion of the tool with respect to the end effector is generated by motor 52, which is disposed within the non-sterile zone. The rotational motion that is generated by the motor is transmitted to the tool via an interface that maintains the seal between the non-sterile and sterile zones.

Referring to FIG. 10A, for some applications, linear tool motor 100 is disposed within the non-sterile zone. Linear tool motor 100 typically drives tool-actuation arm 110 to move linearly. For such applications, tool-actuation arm 110 is typically disposed within the non-sterile zone and is configured to push a portion of a tool (such as a plunger 120 of a syringe) linearly by pushing the portion of the tool through sterile drape 102. For some applications, a portion 114 of the sterile drape that is disposed at the interface between the tool-actuation arm and the portion of the tool that is pushed is configured to have greater rigidity and/or wearability than other portions of the drape. For example, a sticker 116 may be placed at portion 114 in order to enhance the rigidity and/or wearability of the portion relative to other portions of the sterile drape. Or, the drape may be treated (e.g., using a heat treatment, or a chemical treatment) at portion 114 in order to enhance the rigidity and/or wearability of the portion relative to other portions of the sterile drape. Or, the drape may comprise an alternative or additional material at portion 114 as compared to other portions of the drape in order to enhance the rigidity and/or wearability of the portion relative to other portions of the sterile drape. Thus, in the example shown in FIGS. 10A-C, linear motion of a portion of a tool is generated by linear tool motor 100, which is disposed within the non-sterile zone. The linear motion that is generated by the motor is transmitted to the portion of the tool via the drape, such as to maintain the seal between the non-sterile and sterile zones.

Typically, sterile drape 102 is disposed around and sealed with respect to drape plate 104. Typically, drape plate 104 is couplable to the end effector and is coupled to (or couplable to) tool mount 92. When the drape plate is coupled to both the end effector and to the tool mount, then movement of the arms and the end effector (which is generated within the non-sterile zone) is transmitted to the tool mount and to the tool (both of which are disposed within the sterile zone), via the drape plate.

Figure 11A:
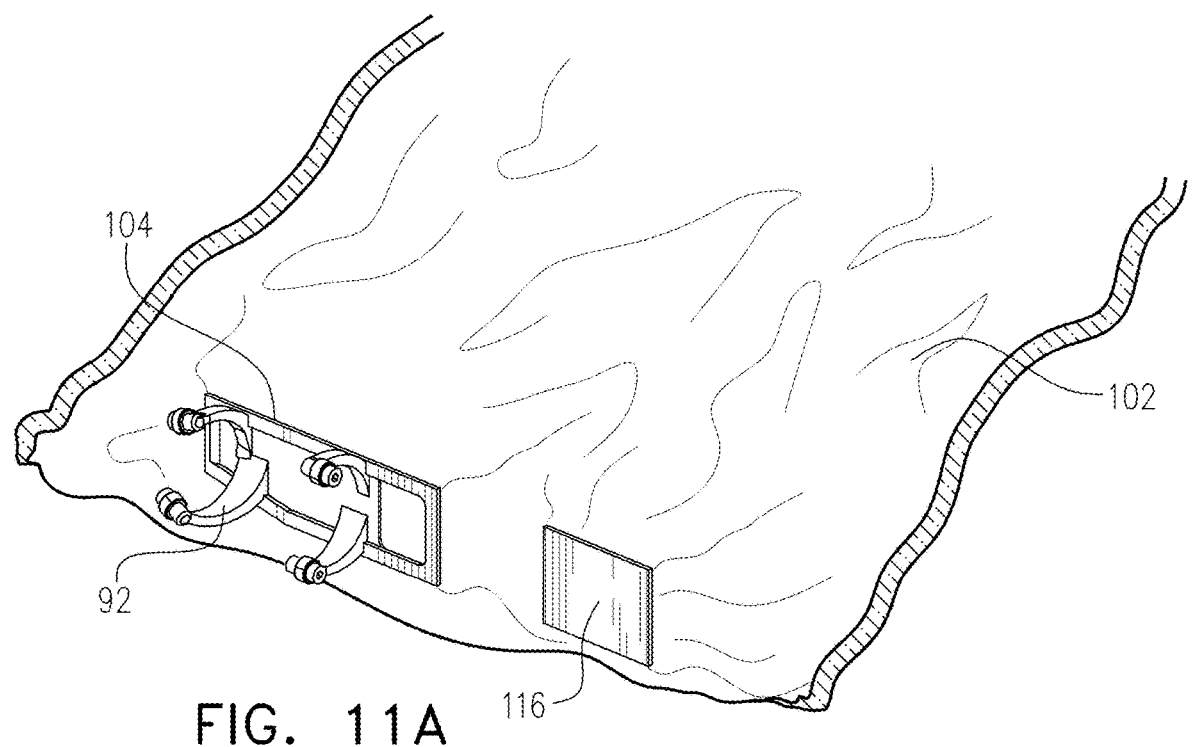
FIGS. 11A and 11B are photographs of a sterile drape and drape plate that are generally similar to those that are schematically illustrated in FIGS. 10A, 10B, and 10C, in accordance with some applications of the present invention.
Figure 11B:
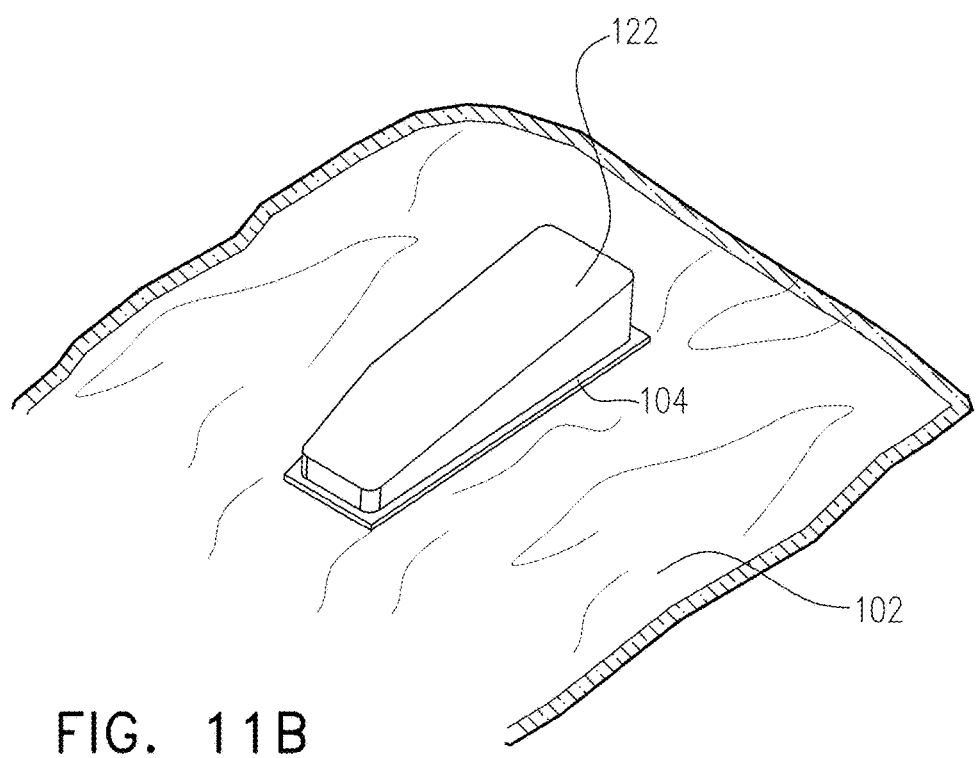

Reference is now made to FIGS. 11A and 11B, which are photographs of a sterile drape 102 and drape plate 104 that are similar to those that are schematically illustrated in FIGS. 10A, 10B, and 10C, in accordance with some applications of the present invention. FIG. 11A is a photograph showing the view of the sterile drape and drape plate from the sterile zone. As may be observed, tool mount 92 is shown, tool mount 92 being built into drape plate 104 in the example that is shown. In addition, sticker 116 is shown. As described above, the sticker is configured to be placed at a portion of the sterile drape that is disposed at the interface between the tool-actuation arm and the portion of the tool that is pushed is configured to have greater rigidity and/or wearability than other portions of the drape. It may also be observed that drape 102 is shaped such as to be placed over arms of a robotic unit. FIG. 11B is a photograph showing the view of the sterile drape and drape plate from the non-sterile zone. As may be observed, the back side of the drape plate is typically shaped to define a housing 122. The housing typically houses gear wheel 54A. Housing portion is typically configured to be coupled to end effector 30 (shown in FIG. 10A), which is disposed at the end of the arms and supports tool motor 52. For example, the housing portion may be coupled to the end effector via a snap-lock mechanism.

Figure 12A:
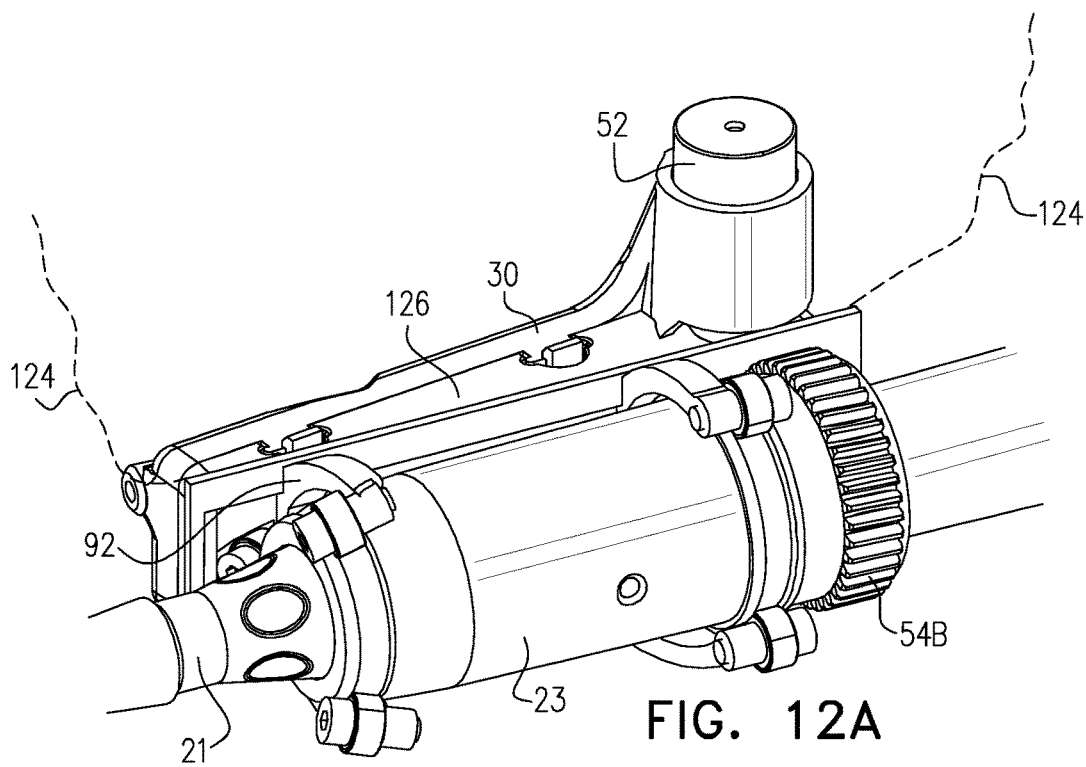
FIGS. 12A and 12B are schematic illustrations of a sterile drape and drape plate for use with a robotic unit that is configured to rotate a tool within the end effector, in accordance with some further alternative applications of the present invention.
Figure 12B:
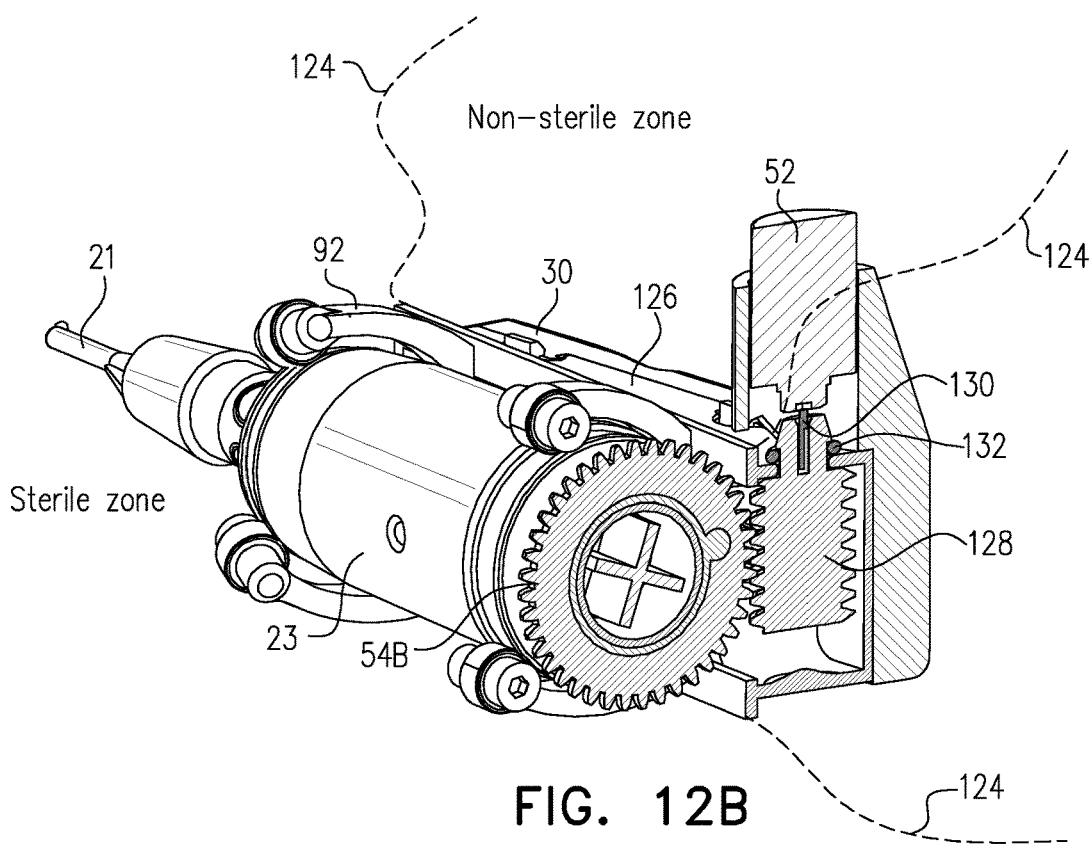

Reference is now made to FIGS. 12A and 12B, which are schematic illustrations of a sterile drape 124 and drape plate 126 for use with a robotic unit in which the tool is rotated within the end effector, in accordance with some further alternative applications of the present invention. The apparatus as shown in FIGS. 12A-B is generally similar to that shown and described with respect to FIGS. 10A-C, except for the following differences. In the apparatus shown in FIGS. 12A-B, tool motor 52 is configured to drive a worm gear 128 to move linearly (e.g., in an up-down direction), in order to drive gear wheel 54B (which is typically built into or coupled to tool 21 or tool sleeve 23) to rotate. As described with reference to FIGS. 10A-C, typically, tool motor 52 is disposed upon end effector 30, which is disposed within the non-sterile zone. Tool motor 52 typically directly drives a linear motion-transmission portion 130 (such as a pin or a shaft) to move linearly (e.g., in an up-down direction). The motion-transmission portion is configured to transmit linear motion of the motor to worm gear 128 and the worm gear drives the tool to rotate with respect to the end effector by driving gear wheel (i.e., spur gear) 54B to rotate. For some applications, the worm gear is disposed within (e.g., built into) the drape plate. Typically, linear motion-transmission portion 130 is mechanically coupled to worm gear 128 in such a manner that the interface between the linear motion-transmission portion and worm gear 128 is sealed such as to maintain a seal between the sterile zone and the non-sterile zone (e.g., via an O-ring 132, as shown in FIG. 12B). Thus, in the example shown in FIGS. 12A-B, motion of the tool with respect to the end effector is generated by motor 52, which is disposed within the non-sterile zone. Linear motion that is generated by the motor is transmitted to the sterile zone via an interface that maintains the seal between the non-sterile and sterile zones. The linear motion is then converted to rotational motion of the tool with respect to the end effector.

Figure 14A:
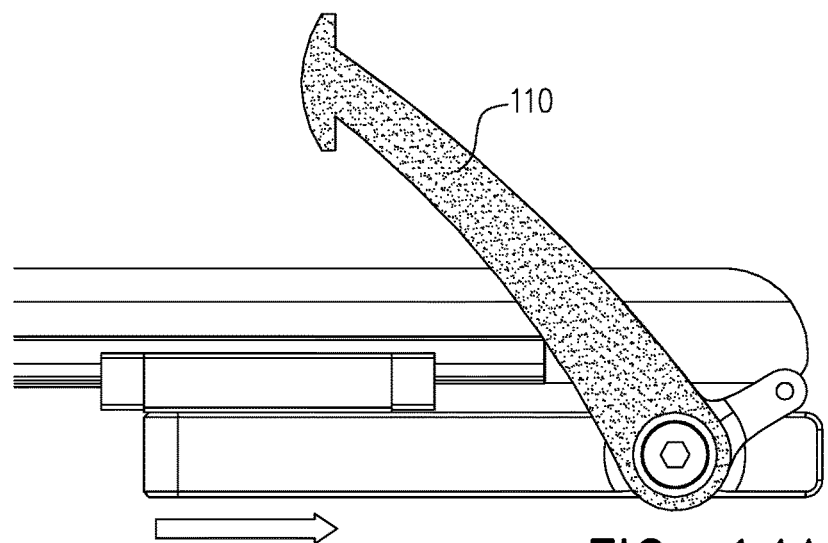
FIGS. 14A, 14B, and 14C are schematic illustrations of the automatically foldable tool-actuation arm at respective stages of its motion with respect to a tool mount, in accordance with some applications of the present invention.
Figure 14B:
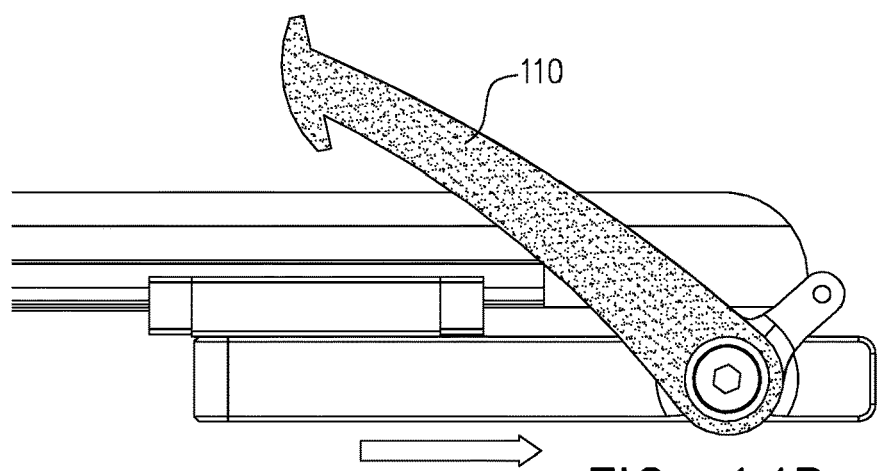
Figure 14C:
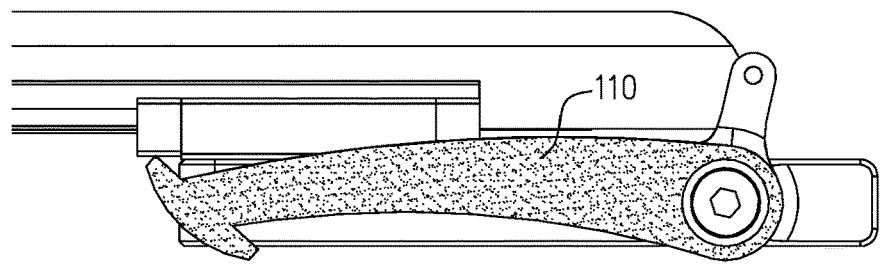

Reference is now made to FIG. 13, which is a schematic illustration of end effector 30 that includes tool-actuation arm 110 for pushing a tool or a portion thereof linearly, in accordance with some applications of the present invention. For some applications, the tool-actuation arm is configured to fold automatically in response to being retracted to a given distance from tool mount 92. Reference is also made to FIGS. 14A, 14B, and 14C, which are schematic illustrations of an automatically foldable tool-actuation arm at respective stages of its motion with respect to a tool holding portion of the end effector, in accordance with some applications of the present invention. As described hereinabove, typically, tool-actuation arm 110 is configured to push a portion of a tool (such as plunger 120 of a syringe) linearly. Typically, linear tool motor 100 drives the arm to move linearly via a transmission shaft 134 (shown in FIG. 13). For some applications, the tool-actuation arm is configured to fold automatically in response to being retracted to a given distance from tool mount 92, as shown in the transition from FIG. 14A to FIG. 14B and then from FIG. 14B to FIG. 14C. In this manner, the tool-actuation arm may be folded automatically such as to accommodate the insertion of a larger tool, such as a phacoemulsification probe, into the tool mount, without requiring removal and/or manual folding of the tool-actuation arm. Typically, the tool-actuation arm is configured to fold automatically by means of an automatic tool-actuation arm unfolding mechanism, such as a spring mechanism, being activated. Further typically, in response to the tool-actuation arm being moved closer to the tool mount, the tool-actuation arm is configured to automatically unfold (e.g., via an automatic tool-actuation arm unfolding mechanism, such as a spring mechanism, being activated). For some applications, rather than being configured to fold automatically, the arm is configured to be moved in a different manner such as to accommodate the insertion of a larger tool, such as a phacoemulsification probe, into the tool mount, without requiring removal and/or manual movement of the tool-actuation arm. For example, the arm may be configured to automatically retracted, e.g., using an electromechanical actuator, a spring mechanism, etc.

It is noted that the scope of the present applications includes combining elements of the sterile drape, the drape plate, and the tool actuation arm that are shown in respective figures with each other. Purely by way of example, the tool actuation arm shown in FIGS. 13-14C can be combined with any one of the examples of sterile drapes and drape plates described with reference to FIGS. 9-12B.

Although some applications of the present invention are described with reference to cataract surgery, the scope of the present application includes applying the apparatus and methods described herein to other medical procedures, mutatis mutandis. In particular, the apparatus and methods described herein to other medical procedures may be applied to other microsurgical procedures, such as general surgery, orthopedic surgery, gynecological surgery, otolaryngology, neurosurgery, oral and maxillofacial surgery, plastic surgery, podiatric surgery, vascular surgery, and/or pediatric surgery that is performed using microsurgical techniques. For some such applications, the imaging system includes one or more microscopic imaging units.

It is noted that the scope of the present application includes applying the apparatus and methods described herein to intraocular procedures, other than cataract surgery, mutatis mutandis. Such procedures may include collagen crosslinking, endothelial keratoplasty (e.g., DSEK, DMEK, and/or PDEK), DSO (descemets stripping without transplantation), laser assisted keratoplasty, keratoplasty, LASIK/PRK, SMILE, pterygium, ocular surface cancer treatment, secondary IOL placement (sutured, transconjunctival, etc.), iris repair, IOL reposition, IOL exchange, superficial keratectomy, Minimally Invasive Glaucoma Surgery (MIGS), limbal stem cell transplantation, astigmatic keratotomy, Limbal Relaxing Incisions (LRI), amniotic membrane transplantation (AMT), glaucoma surgery (e.g., trabs, tubes, minimally invasive glaucoma surgery), automated lamellar keratoplasty (ALK), anterior vitrectomy, and/or pars plana anterior vitrectomy.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 28. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W), DVD, and a USB drive.

A data processing system suitable for storing and/or executing program code will include at least one processor (e.g., computer processor 28) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the algorithms described herein, can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 28) or other programmable data processing apparatus, create means for implementing the functions/acts specified in the algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the algorithms described in the present application.

Computer processor 28 is typically a hardware device programmed with computer program instructions to produce a special purpose computer. For example, when programmed to perform the algorithms described with reference to the Figures, computer processor 28 typically acts as a special purpose robotic-system computer processor. Typically, the operations described herein that are performed by computer processor 28 transform the physical state of a memory, which is a real physical article, to have a different magnetic polarity, electrical charge, or the like depending on the technology of the memory that is used. For some applications, operations that are described as being performed by a computer processor are performed by a plurality of computer processors in combination with each other.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for performing a procedure on a portion of a body of a patient using a robotic unit that includes an end-effector, tool mount configured to hold a tool such that the tool is coaxial with the end effector, and a linear tool motor configured to drive at least a portion of the tool to move linearly with respect to the end effector, the apparatus comprising:
   a tool-actuation arm configured to be moved linearly by the linear tool motor, to thereby move at least the portion of the tool linearly with respect to the end effector; and
   an automatic tool-actuation arm folding mechanism that is configured to cause the tool-actuation arm to fold automatically in response to being retracted to a given distance from the tool mount.

2. The apparatus according to claim 1, wherein the automatic tool-actuation arm folding mechanism comprises a spring mechanism.

3. The apparatus according to claim 1, wherein the tool includes a syringe that includes a plunger, and wherein the tool-actuation arm is configured to push the plunger of the syringe linearly.

4. The apparatus according to claim 1, wherein the tool-actuation arm is configured to fold such that the tool mount is able to accommodate a large tool without requiring removal and/or manual folding of the tool-actuation arm.

5. The apparatus according to claim 1, wherein the robotic unit is configured for performing cataract surgery using a plurality of tools that include a phacoemulsification probe, and wherein the tool-actuation arm is configured to fold such that the tool mount is able to accommodate the phacoemulsification probe without requiring removal or manual folding of the tool-actuation arm.

6. The apparatus according to claim 1, further comprising an automatic tool-actuation arm unfolding mechanism configured to cause the tool-actuation arm to automatically unfold in response to the tool-actuation arm being moved closer to the tool mount.

7. The apparatus according to claim 6, wherein the automatic tool-actuation arm unfolding mechanism comprises a spring mechanism.

8. A method for performing a procedure on a portion of a body of a patient using a robotic unit that includes an end-effector, a tool mount that is configured to hold a tool such that the tool is coaxial with the end effector, and a linear tool motor configured to drive at least a portion of the tool to move linearly with respect to the end effector, the method comprising:
   driving a tool-actuation arm to move linearly, to thereby move at least the portion of the tool linearly with respect to the end effector; and
   causing the tool-actuation arm to fold automatically by driving the tool-actuation arm to become retracted to a given distance from the tool mount, such as to actuate an automatic tool-actuation arm folding mechanism.

9. The method according to claim 8, wherein the automatic tool-actuation arm folding mechanism comprises a spring mechanism.

10. The method according to claim 8, wherein the tool includes a syringe that includes a plunger, and wherein driving the tool-actuation arm to move linearly comprises pushing the plunger of the syringe linearly.

11. The method according to claim 8, wherein causing the tool-actuation arm to fold comprises accommodating a large tool within the tool mount without requiring removal or manual folding of the tool-actuation arm.

12. The method according to claim 8, wherein causing the tool-actuation arm to fold comprises accommodating a phacoemulsification probe within the tool mount without requiring removal or manual folding of the tool-actuation arm.

13. The method according to claim 8, further comprising actuating an automatic tool-actuation arm unfolding mechanism configured to cause the tool-actuation arm to automatically unfold by driving the tool-actuation arm to move closer to the tool mount.

14. The method according to claim 13, wherein the automatic tool-actuation arm unfolding mechanism comprises a spring mechanism.

* * * * *